United States Patent
Dollansky

[11] Patent Number: 5,585,636
[45] Date of Patent: Dec. 17, 1996

[54] CHARACTERISTIC ABSORPTION

[75] Inventor: Erich Dollansky, Kissing, Germany

[73] Assignee: Karl Stefan Reiner, Austria

[21] Appl. No.: 353,504

[22] Filed: Dec. 9, 1994

[30] Foreign Application Priority Data

Dec. 10, 1993 [DE] Germany ............... 43 42 246.2

[51] Int. Cl.⁶ ............... G01N 21/31; G01N 21/61; G01J 3/427
[52] U.S. Cl. ............... 250/343; 250/345; 356/437
[58] Field of Search ............... 250/343, 345, 250/338.5; 356/437, 436, 439

[56] References Cited

U.S. PATENT DOCUMENTS

| | | | |
|---|---|---|---|
| 4,266,131 | 5/1981 | Ahjopalo et al. | 250/345 X |
| 4,525,069 | 6/1985 | Tanaka et al. | 356/435 |
| 4,673,812 | 6/1987 | Yoneda | 250/343 X |
| 4,737,652 | 4/1988 | Faschingleitner et al. | 250/575 |
| 4,925,299 | 5/1990 | Meisberger et al. | 356/40 |
| 5,002,391 | 3/1991 | Wolfrum et al. | 356/307 |
| 5,113,073 | 5/1992 | Szepan | 250/343 |
| 5,149,983 | 9/1992 | Kaiblinger | 250/575 |
| 5,173,749 | 12/1992 | Tell et al. | 250/343 X |
| 5,332,901 | 7/1994 | Eckles et al. | 250/343 X |

FOREIGN PATENT DOCUMENTS

| | | |
|---|---|---|
| 0197917 | 4/1986 | European Pat. Off. . |
| 0244721 | 4/1987 | European Pat. Off. . |
| 0318752 | 11/1988 | European Pat. Off. . |
| 3106331 | 9/1982 | Germany . |
| 3218102 | 12/1982 | Germany . |
| 3615259 | 11/1987 | Germany . |
| 3726524 | 2/1989 | Germany . |
| 3808445 | 9/1989 | Germany . |
| 3819531 | 12/1989 | Germany . |
| WO8912222 | 12/1989 | WIPO . |
| WO9204614 | 3/1992 | WIPO . |

Primary Examiner—Carolyn E. Fields
Assistant Examiner—Edward J. Glick
Attorney, Agent, or Firm—Leydig, Voit & Mayer, Ltd.

[57] ABSTRACT

Apparatus and methods for monitoring characteristic absorption of a substance in a mixture include applying radiation pulses with a wavelength characteristic of the substance to be measured and a wavelength uncharacteristic of the substance to a measuring path and to a reference path without the substance mixture. The difference of signals generated between the measuring path and the reference path are conditioned to provide a measurement value.

19 Claims, 27 Drawing Sheets

CHARACTERISTIC ABSORPTION

FIELD OF THE INVENTION

This invention relates to methods for evaluating characteristic absorption of a gas in a mixture and to methods for stabilization of a radiation source used in the evaluation, as well as apparatus for implementing such methods.

BACKGROUND OF THE INVENTION

In many fields the weakening of radiation—i.e., wave radiation,—in interaction with matter, provides the basis of measuring applications, where a part of the radiation is absorbed or weakened. The remainder is reflected or passed through the matter under observation. Depending on the characteristics and composition of the matter, radiation with a certain energy or wavelength, is completely absorbed or weakened. The absorbed energy is characteristic for the matter being analyzed. This characteristic absorption is typically evaluated to determine the characteristics of the radiated matter. For example, the elements in a compound may be determined with high accuracy. In addition, the concentration of a substance in a compound may be determined from the level of weakening of the characteristic radiation.

In electronic evaluation of transmitted or reflected signals weakened by characteristic absorption, the signal portions which are caused by disturbances of the measuring device, particularly the radiation source, and the signal portions caused by the absorption of the matter to be analyzed must be differentiated. In known procedures, particularly with low concentrations of the matter to be analyzed, the absorption signal is often superimposed by the noise of the measuring device. Improved resolution capacity can only be achieved with significant expenditures on instrumentation.

For example, EP 89 906 096.6 describes a method for determining the concentration of a gas in a gas mixture by applying a pulsated light of a laser, whose wavelength is switched after every pulse, and sent through the measuring path. One wavelength, or absorption wavelength, is characteristic for a gas whose concentration must be determined; the other wavelength is not characteristic for any substance which is located in the measuring path. The light pulse whose wavelength is characteristic for a selected gas is slightly weakened in the measuring path by the characteristic absorption.

With very low concentrations or short measuring paths, however, the useful signal becomes so small that it cannot be evaluated. It disappears in the noise of the overall system. In addition to the noise components generated from light detectors and associated electrical circuitry, there are significant noise components inherent to the laser radiation apparatus itself. For example, noise sources in the laser may be generated by the power supply, changes in pressure or temperature of the emission, and the influence of laser cooling, which may have been used on the emission. Depending on the laser type, this noise component may be minimized with significant expenditures in instrumentation, however, it can never be eliminated completely.

A problem in known procedures for determining the ammonia concentration in smoke gasses, is their sensitivity—the so-called cross-sensitivity—in relation to other smoke gas components. Particularly in waste incinerator installations, the smoke gas consists of many different substances. For example, many different hydrocarbon compounds from plastics incineration provide a wide spectrum of substances in the smoke gas.

SUMMARY OF THE INVENTION

This invention relates to methods that minimize disturbing influences on a measured value. The measured value is established from the difference of signals of two paths, a reference path and a measured path. The differential signal obtained is preferably conditioned as a function of frequency and/or time before it is passed as the corrected measured value in order to improve the measuring quality.

The invention may be implemented with a radiation source, particularly a laser, that emits radiation of more than two wavelengths. Signals are formed electronically, which only consist of the electric signals of two light pulses. A detected signal comprised of more than two pulses is divided into several signals, where each signal consists of one characteristic and one uncharacteristic pulse.

The difference signal is preferably derived at a time that the signal level of the characteristic signal pulse is maximum and at the time in which the uncharacteristic signal pulse is maximum, and is finally provided as the measured value.

In an additional aspect the signals of the measuring path and the reference path are assessed and corrected before the measured valued is established—preferably from the difference between measured and reference path signals.

Preferably, in a measuring cycle, the concentration of a substance is also measured, which is responsible for the cross-sensitivity, and with this measuring result, the actual measuring result is corrected.

The combination of the two above mentioned preferred aspects of this invention, disturbance suppression and establishment of measured value, provides a significant improvement of the known concentration measuring procedures using laser radiation of individual gases in a gas mixture or similar analysis.

In addition, individual pulses of the electric signal may be analyzed for disturbances and, if necessary, it is corrected prior to establishment of the measured value. By establishing the difference from the signal of the measuring path and the excitation signal, the influence of the light source and all other disturbing sources in the measuring system itself are minimized to the measured value. Subsequently, this differential signal is selected in the frequency domain and/or in the time domain analyzed again, and corrected before if necessary prior to passing the measured value.

If, during measurement, cross-sensitivities to other substances appear, the method of the invention may include applying additional light pulses, whose wavelengths are characteristic for the additional gases, in a sequence comprising several pulses. Upon detection of signals from this signal sequence, subsequent signal processing takes place according to the manner described above. A measured value for each characteristic light wavelength is thereby obtained. The influence of the other substances on the actual measured value—the concentration of the selected gas—may then be eliminated.

Another specific aspect of the invention is the stabilization of the radiation source, particularly laser stabilization, which is divided into automatic start-up and long term stabilization modes. Start-up mode stabilization utilizes rectifier circuitry in the reference path. For the long term stabilization, sample-and-hold circuitry is used.

Preferably, there is a signal division, such that at least one calibration path signal and the reference signal are provided to the radiation source stabilization circuitry, and one signal pair from reference and measuring path signals are subject to analysis, and if necessary, corrected.

At the same time, the invention provides a solution of the cross-sensitivity problem. If the problem of cross-sensitivity occurs fundamentally during measurement, the laser may be adjusted so that it emits at least three lines. Also, additional vessels are each brought into one calibration path where the substance which causes the cross-sensitivity is located.

In the description below it is assumed that there is an additional vessel to balance the cross-sensitivities. Basically, the procedure does not change if more vessels are used to correct the cross-sensitivity. Per each additional vessel one additional characteristic light pulse is created and one additional circuit to establish and correct the measured value is inserted. The signal timing must be adjusted accordingly. If no correction of the cross-sensitivity is desired, the vessel and the related signal processing may be eliminated without substitution.

BRIEF DESCRIPTION OF THE DRAWINGS

Further advantages and developments of the invention are yielded from the following description of preferred examples of carrying out the invention. In this regard, reference is made to the attached drawings in which.

DETAILED DESCRIPTION OF THE PREFERRED EMBODIMENTS

Figure 1:
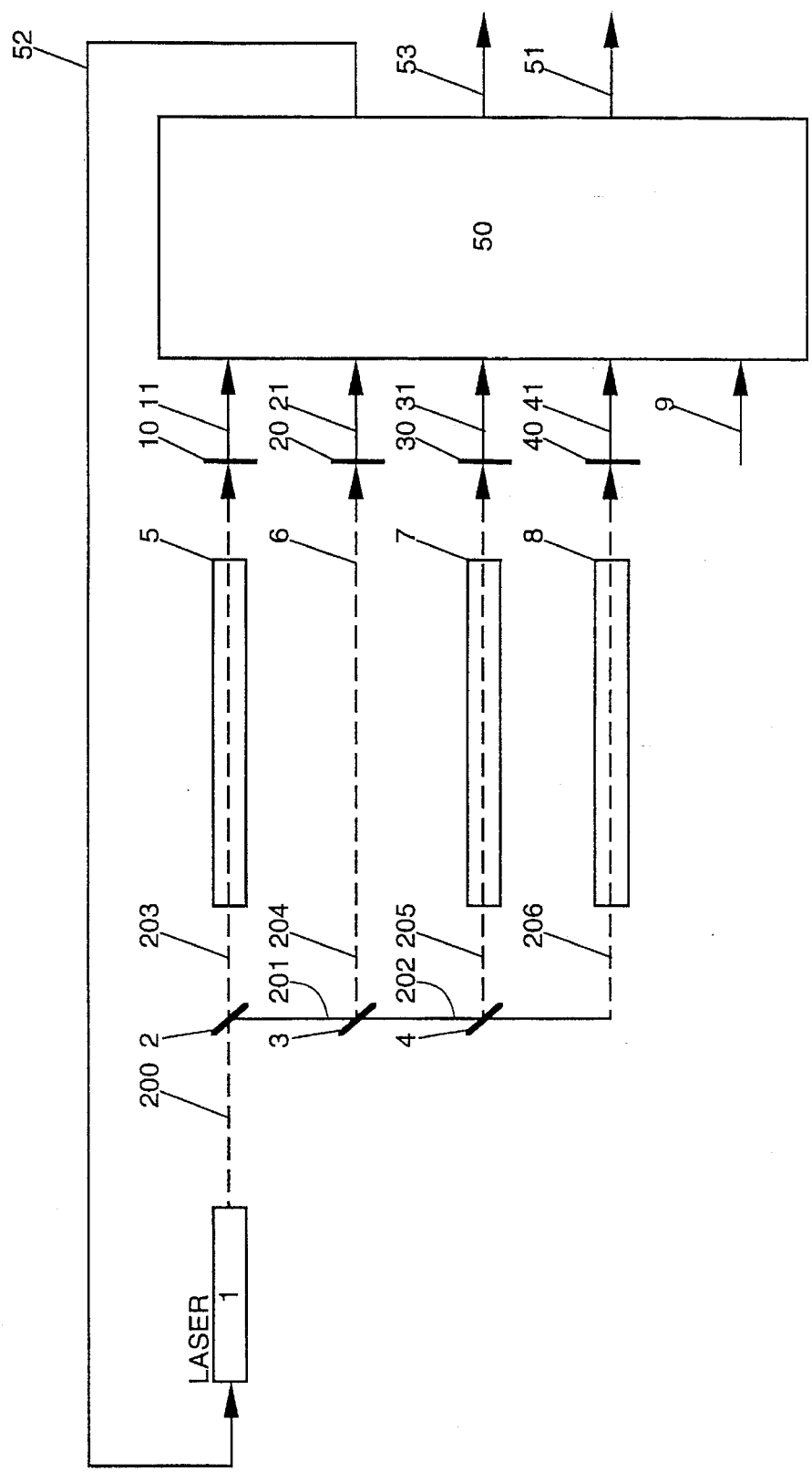
FIG. 1 shows the overall construction of an example of implementation of the invention for the determination of concentration gases in a gas mixture.

This invention may be used, for example, in power plants to analyze waste gases. Thermal power plants produce the nitric oxides which are harmful to the environment. Ammonia is used to reduce these effects, but is also a substance which harms the environment. This invention permits the ammonia injection to be done very accurately so that, on the one hand, extremely few nitric oxides exit the smoke gas channel, and on the other hand, only a minimal amount of ammonia exits.

In addition, the invention—particularly due to the reduced cost of instrumentation required and to the resultant high measuring accuracy—may be applied to particular advantage for fraud protection of check cards and for access control. If a plastic card, e.g. a check or credit card, is coated in part with a certain substance, a definite identification may be made with this invention. If the coating is such that it cannot be identified by the human eye or other, less sensitive measuring devices, a high degree in fraud protection is achieved.

Another particularly advantageous application of the invention is the mixture control in continuous processes. Known procedures typically employ discontinuous mixing in order to produce substance mixes with low concentration fluctuations. The individual components are placed together in a container, mixed and subsequently the container is emptied. This invention, however, permits the substance composition to be continuously monitored during the mixing process and the amount of individual substances to be added may be adjusted accurately to address the actual needs.

The simple construction is particularly advantageous: The invention is based on in an installation to determine the concentration of gasses in a gas mixture—on a system, consisting of a radiation source, particularly a laser, one or several calibration vessels disposed in a calibration path, a reference path and a measuring path. The laser in particular emits light with at least two different wavelengths. One wavelength is characteristic for a selected substance, another wavelength is uncharacteristic for all substances in the measuring path. The other light wavelengths which may be used are characteristic for the other substances. All wavelengths used are uncharacteristic for all other substances which may be in the measuring path and whose concentration is variable.

The laser is controlled such that it alternately emits light of the selected wavelengths. Short emission pauses or emission reductions, are inserted between the light pulses. Upon completing one emission sequence, a sequence is initiated. In order to simplify the laser control the laser may then be controlled such that it reverses the sequence in which the various light wavelengths are emitted at the end of a sequence. This must be taken into account in the evaluation and correction circuitry utilized.

The light of the laser is dissected into three or more rays via a ray divider. One ray each simultaneously runs through the reference path, the measuring path and the calibration path(s). Therefore, the rays are almost identical in their intensity curve. Deviations result primarily only from the spectral characteristics of the ray dividers which are used. The electric signals vary slightly due to the spectral characteristics of the detectors.

The light in the reference path is led directly to a detector. There is only air in the reference path. It is preferably free of the gas whose concentration is to be determined in the measuring path and which is also contained in one calibration vessel. The light in the calibration path is led through a calibration vessel to a detector. In the calibration vessel, there is a known amount of the substance whose concentration is to be determined on the measuring path. The concentration of the selected gas and the absolute pressure in the vessel are selected such that the light ray with the characteristic wavelength is weakened significantly, as close as possible to 100%. In additional calibration vessels which may be present, there are substances which may be on the measuring path and which may have an invalidating influence on the measured result. The light in the measuring path is impinged on a measuring section. In the measuring section, there is a gas mixture which may contain that gas whose concentration must be determined.

With light wavelengths around 10 μm, a $CO_2$ isotope laser is suitable as the light source. In this range there are some wavelengths characteristic for ammonia which are not characteristic for other typical components of smoke gas.

In the detectors an electric signal is developed from the received light signal, proportional to the intensity of the impinging light energy. Therefore, the signal of the detector developed in the reference path directly corresponds to the laser emission. The signal proximate the calibration path corresponds to the laser emission when the laser emits light with the uncharacteristic wavelength. When the laser emits light with the characteristic wavelength, the signal developed by this detector appears weakened. Because the concentration in the calibration vessel does not change, the weakening always remains the same. The signal proximate the measuring path corresponds to the laser emission when the laser emits light with the uncharacteristic wavelength. When the laser emits light with a characteristic wavelength, the signal on the detector always appears weakened. The weakening is proportional to the concentration of the selected gas—a gas, which is also in one of the calibration vessels—on the measuring section.

The signals of the detectors are supplied to analyzing and evaluation circuitry to establish the measured value from the differential signal between measuring path signal and reference path signal. The evaluation circuitry provides the measured value signal, a measured value signal corresponding to the reliability of the measured value, and preferably a signal for the radiation source stabilization circuitry. The evaluation circuitry preferably also receive information about the current status of processing.

The signals of all detectors are preferably scaled to a uniform signal level with amplification and filter circuitry and relieved from undesired signal components. Subsequently, the signals are preferably divided. The signals from the reference path and the calibration paths are supplied to source stabilization circuitry, which processes the signals such that the system control can create the appropriate signal for source control.

The signal from the reference path and the signal from the measuring path are also preferably supplied to an evaluation and correction circuitry. This first evaluates a signal pulse by comparing it to stored reference values and corrects the signal pulse, if necessary. If more than one calibration vessel is provided in the system, new signal pairs are created from an input signal pair, which, within one signal period, contain only two different signal pulses. Each of these signal pairs is subsequently supplied to the correction circuitry circuit to establish and correct the measured value.

The measured value establishment circuitry preferably contains a subtractor to form a differential signal, to which at least two sample-and-hold circuits are connected which sample the differential signal in the middle of the characteristic and the uncharacteristic signal pulse, and an additional subtractor to provide the difference between the differential signal at the moment of maximum of the characteristic and at the moment of maximum of the uncharacteristic signal pulse. These measured value establishing and correcting circuits create a signal from its signal pair which is proportional to the concentration of the respective gas on the measured section. The system control forms the measured value from the data of the measured value establishing and correcting circuits and the current processing data, and a measure for the reliability of the measured value. All waveforms in the evaluation circuitry are coordinated via a phase generator. The display pattern of the phase generator is selected by the system control.

Amplifier and filter: Behind all detectors there is a signal processing installation, consisting of amplifier and filter. The output level of the detector signal is amplified to a uniform level and the signals are subsequently relieved from undesired signal parts by ways of a low pass filter. The cutoff frequency of the filter is adjusted such that the ripple of the filter does not unintentionally invalidate the information content of the signal. With only one calibration vessel, this means that, independent of the selected filter type, the filter must be adjusted such that it does not influence the signal at the pulse beat frequency and the half pulse beat frequency.

Phase generator: The phase generator supplies all function groups of the evaluation electronics with synchronous phase signals. The phase generator is constructed such that the system control may influence the phase position of each individual phase.

Signal analysis: In the evaluation and correction installation the two input signals from the measuring path and reference path detectors are digitalized and moved to the digital evaluation and correction installation. When the correction is completed, it emits the signals via digital/analogous convertor to the electronics which are connected in series.

By means of a required value storage the evaluation and correction installation is in a position to recognize the required curve and to change the detector signal accordingly. With statistical methods the evaluation and correction installation recognizes even the required curve form and files it in the required value storage.

If more than one characteristic light wavelength is provided, the signal evaluation also includes a division of the input signals into signal pairs which consist only of two pulses within a signal period.

Measured value establishment and correction: The measured value is derived from the difference between the corrected measuring signal and the corrected reference signal. This signal is amplified and filtered and moved to two sample-and-hold circuits. The sample-and-hold circuits are activated by two phase signals at the maximum of one each signal pulse of the input signal. The two output signals are each moved to an additional sample-and-hold circuit and to a circuit for tolerance assessment. This tolerance assessment activates the above mentioned second sample-and-hold step. The tolerance assessment is synchronized by the phase generator with the input signal of the measured value establishment. The tolerance assessment receives the information about the admissible tolerance from the system control in the input signal. The system control derives the currently admissible tolerance from the status of the process.

The difference is derived from the output signal of the second sample-and-hold step. Following an additional amplification and filtering the signal is moved to the system control for further processing.

In addition, the analysis circuitry is preferably equipped with a device to process the signal for radiation source stabilization with rectifier and sample-and-hold circuits, which sample the reference and calibration signals at a preset moment, in order to determine the waveshape, the phase position, as well as the maximum value and the average value per signal period.

Another preferred design example consists of an evaluation and correction circuitry. In the evaluation and correction circuitry, the signals from the measuring path and the reference path are digitized and compared with a reference signal which is located in a reference value storage, and corrected, if necessary. Evaluation takes place over a complete period. The signal is completely sampled and temporarily stored within one period.

The signal from the reference path is only subject to disturbances which are caused in the system itself. The same disturbances are also present in the measuring path signal. In the signal from the measuring path additional disturbances are present due to the unintentional changes of the light emission on the measured section, i.e., by turbulence or dust.

Without disturbances all signal pulses follow the signal curve shown which is also stored in the reference value storage for signal evaluation. Independent of the actual signal amplitude the form always remains the same. In the steady-state system each pulse may be standardized. For the various pulses, respective different standardization factors must be provided. The evaluation and correction circuitry compares the standardized pulses with a stored reference pattern. A waveshape is in order if it lies within the preset tolerance width and if its first derivation also remains within the tolerance width for the first derivative.

If the signal in the measuring path fails or if it is noticeably disturbed, the evaluation and correction installation keeps emitting the prior signal until the input signal is undisturbed again. The system control is informed that no signal is transmitted which is obtained directly from the measuring path.

At the same time the signal evaluation divides the signal curve into several signals for a separate evaluation. The circuitry to establish and correct a measured value can only evaluate a signal which consists of two different pulses. Before conversion into an analog signal, the evaluation and correction circuitry divides the digital data stream such that only signal pairs are created which consist of one pulse which was created by the uncharacteristic radiation, and one pulse which was created by a characteristic radiation.

In the example described above the signal period of the input signal consists of three signal pulses. One signal pulse is caused by the light pulse whose light wavelength is uncharacteristic for all substances. The two other pulses are caused by light pulses whose wavelength is characteristic for one substance each.

The division takes place such that the period of the new signal, consisting of two pulses, corresponds to the period of the original signal. Also, the amplitude of the pulses remains unchanged. Each individual pulse is then expanded so that its duration corresponds exactly to a half period. The first pulse is supplied at the beginning of the period, the second pulse is supplied starting in the middle of the period.

If the laser is controlled such that its emission spectrum is sampled once from low to high wavelengths and the reverse occurs in the following period, this must be taken into account for the signal division.

If, due to special characteristics, the laser emits more laser lines than scheduled, the additional signal pulses may be electronically suppressed in the evaluation and correction circuitry, provided that the laser, correctly adjusted, is always emitting on these lines. If these undesired signal pulses are to be electronically suppressed, it must be assumed that the laser emits on these lines when the layout of the input amplifier and the laser stabilization are designed. These additional signal pulses must be treated like the characteristic signal pulses to correct the cross-sensitivity. In the evaluation and correction circuitry, these signal pulses are suppressed, i.e. they are also treated like the signals to correct the cross-sensitivity, except that there is no output with an existing signal pair. This achieves that the actual undesired signal pulses are used for signal evaluation and correction. However, they are no longer present in the actual establishment of the measured value and thus are unable to disturb the measured result.

Measured value establishment and correction: Due to the division of the signal with three or more signal pulses into several signals with only two signal pulses each, the system, as relates to the measured value establishment, only consists of one measuring path, one reference path and one calibration path. The system control combines the information of the various installations to establish the measured value into one signal, the measure for the concentration of a selected substance in the measured section.

The measure for the concentration of the selected substance results from the difference of the signal from the reference path and from the measuring path.

If light is emitted by the laser whose wavelength is not characteristic for any gas in the measured section, the light emitted in the measured section is not damped. In principle, the light ray is not damped on the reference path. If the two signals from the reference path and from the measuring path are adjusted to the same level during emission of the uncharacteristic light wavelength, this results in a difference between both signals during emission of the characteristic light wavelength, because the light ray on the measured section is damped in proportion to the concentration of the selected gas. The signal difference is proportional to the damping of the light ray in the measured section.

In this procedure, the disturbances in both signals which are caused by the light source itself, do not lead to signal components in the measured value because they are present in both detector signals with the same amplitude.

For further evaluation the signal level of the differential signal is now sampled at two intervals via two sample-and-hold circuits. The two intervals are selected such that the level difference in the differential signal is maximum. This is the case when a relative maximum occurs in the reference signal at the beginning of the measured value.

The output signals of these two sample-and-hold circuits are moved to an additional sample-and-hold circuit and to the tolerance circuit. The tolerance assessment provides data corresponding to the signal levels of the former sample-and-hold circuits. This data is passed only if the changes in the sampled signal remain within preset limits and the passing is permitted by the system control.

If the measuring signal in the measured section is disturbed, e.g., by a dust cloud, a significant change occurs in the signal. The change results in a maximum in the first derivative of the signal. The tolerance assessment recognizes the change and does not pass the actual measured value. Therefore, the prior measured data is supplied by the sample-and-hold circuits. The system control receives information that the data transfer is blocked. Because the duration of these disturbances is short compared to the dead time in the smoke gas chimney, this method does not result in a recognizable invalidation of the measured value.

Balancing the cross-sensitivities: If the laser is adjusted such that it emits light from more than two wavelengths, a cross-sensitivity to other substances in the measured section may also be recognized and corrected. Thus, a laser is adjusted so that it also emits light with a wavelength which is characteristic for the other substance. In the installation for signal evaluation the input signals are divided into at least two signal branches. One signal branch contains those signals which are caused by the desired substance; an additional signal branch contains those signals which are caused by the undesired substance. A separate evaluation now takes place in each signal branch. This determines the concentration of the desired gas. The measured value obtained, however, is invalidated by the cross-sensitivity to the other substance. Also, the concentration of the undesired substance is determined.

From the concentration of the undesired substance the signal invalidation in the other branch may now be determined. When the measured value has been corrected the system control can supply a measured value which is free of influences from the other substances in the measured section.

It is particularly advantageous in the use in a power plant to determine the ammonia concentration in the waste gas because the evaluation of the obtained measured values may be improved with the known process parameters (operating condition of the measured section).

As long as the total system—in the case of a power generating station this is the total power generating station—is in a stable state, the measuring values cannot be subject to any severe fluctuations. If fluctuations nevertheless appear, then it is better to revert to older measurement values. During the setting in operation and also during the switching-off, however, relatively great fluctuations in measurement values can arise without their cause lying in measurement errors.

The full composition of the fuel has an influence on the flue-gas composition. Changes in the flue-gas composition lead, therefore, to higher admissible fluctuations in the measurement values.

The waste-gas temperature determines the transformation rate of the nitric oxide and therewith the ammonia leakage in the exhaust gas. With temperature fluctuations, therefore, greater fluctuations in the ammonia concentration are expected. Changes in the amount of ammonia spilled-in, therefore, likewise increase the admissible deviations in the measurement values.

Fluctuations in the power delivery of the power plant likewise cause increased fluctuations in the measurement value.

If one of the above-mentioned operating states arises, the system control raises the admissible fluctuation range of the measurement value. When the whole system has again reached a stable state, the admissible fluctuation range in the measurement value is again narrowed by the system control.

Further, preferably there is provided a balancing of the beam dividers: The optical properties of the beam dividers are dependent on the wavelength of the impinging light beam. Although the differences in the wavelengths used are not very great, by reason of the high sensitivity of the present process a clear influence is perceptible. This effect can be utilized for the automatic adjustment of the beam dividers.

For the adjustment of the beam dividers, the laser is set firmly on the requisite light wavelengths. The beam dividers are mounted on a fixed carrier in such manner that they are individually adjustable freely into the two possible angular coordinates and the two possible angular coordinates by means of electromechanical adjusting devices.

After the rough setting of the beam divider has taken place, the input amplifier is set on a fixed output level. Beginning with the beam divider most remote from the light source, the beam dividers are now adjusted individually. A beam divider is optimally adjusted when the amplitudes of the individual signal pulses differ from one another as little as possible and the average level of all the pulses of a signal period assumes a maximum.

Finally it is pointed out that the methods described here for the electrical signal evaluation as well as radiation-source stabilization are not to be understood as restricted to excitation by a light beam of a laser. In principle, any radiation source and type of radiation can be used for which detectors and beam dividers are on hand which behave like the components described here. Also, instead of the monochromatic radiation source there can be used a radiation source with a broad emission spectrum and by means of filtering the requisite radiation spectrum can be filtered out.

FIG. 1 shows the overall construction of a device for the concentration determination of gases in a gas mixture according to the invention. This case of application is described as an example, and is by no means to be understood as restrictive. As noted above, the invention is suited for all processes of detection and concentration determinations that are based on characteristic absorption by the solid or gaseous substance to be measured.

As shown in FIG. 1, a laser 1 generates monochromatic light of at least three wavelengths. One wavelength is characteristic for a gas which is present in a vessel in a first calibrating path 7. Another wavelength is characteristic for a gas which is present in a vessel in a second calibrating path 8. A third wavelength is uncharacteristic for all substances that can be present at a measuring path 5. In the preferred embodiment, laser 1 emits light of the wavelengths described in alternation. Between the emissions there can be inserted pauses or weakening phases.

The light beam 200 of the laser 1 passed to a beam divider 2. The beam divider 2 subdivides the light beam 200 into light beams 201 and 203. The light beam 203 passed over the measuring path 5 to a detector 10. When light with the uncharacteristic wavelength is emitted from laser 1, no change of the light beam occurs on the measuring path When light having a wavelength characteristic for the substance in the path 7 is emitted from the laser 1, the light beam is attenuated proportionally to the concentration of this substance on the measuring path 5. If light having a wavelength characteristic for the substance in path 8 is emitted from the laser 1, then the light beam is attenuated proportionally to the concentration of this substance on the measuring path 5. The detector 10 transforms the impinging light beam into an electrical signal having an amplitude proportional to the incident radiation intensity. This signal is supplied to an evaluating electronic unit 50 via a line 11 for further processing.

The light beam 201 is passed to a beam divider 3. The beam divider 3 subdivides the light beam 201 into the light beams 202 and 204. The light beam 204 is passed over the reference path 6 to a detector 20. The light beam is not altered on the reference path 6. The detector 20 transforms the impinging light beam 204 into an electrical signal, the amplitude of which is also proportional to the impinging radiation intensity. This signal is supplied to the evaluating electronic unit 50 over a line 21 for further processing.

The light beam 202 is thereafter passed to a beam divider 4. The beam divider 4 subdivides the light beam 202 into light beams 205 and 206. The light beam 205 is passed over the calibrating path 7 to a detector 30. As noted above, the calibrating path 7 includes a vessel filled with a substance the concentration of which on the measuring path 5 is to be determined. The detector 30 transforms the impinging light beam into an electrical signal, the amplitude of which is proportional to the impinging beam intensity. This signal is fed over a line 31 to the evaluating electronic unit 50 for further processing.

The light beam 206 is passed over the calibrating path 8 to a detector 40. The calibrating path 8 includes a vessel is filled with a substance which can be present on the measuring path 5 and which hampers the error-free concentration determination for the substance in the calibrating path 7. The detector 40 transforms the impinging light beam into an electrical signal having an amplitude is proportional to the impinging radiation intensity. This electrical signal is fed over a line 41 to the control unit 50 for the further processing.

The control unit 50 supplies control signals to the laser 1 via a line 52 such that the laser 1 emits light of the characteristic wavelength of the substance in the calibrating path 7, light of the characteristic wavelength of the substance in the calibrating path 8, and light uncharacteristic for all the substances on the measuring path 5, in an alternating fashion.

The control unit 50 receives input signals concerning the current operating state of the measuring path on a line 9. This contains information about pressure, temperature, oxygen content, fuel composition, current ammonia injection amount and known analysis values of the flue gas composition on the measuring path 5.

The control unit 50 supplies an output signal indicative of concentration of the substance on the measuring path 5, which is present also in the calibrating path 7, on a line 51. The control unit also supplies an output signal on line 53 indicative of the dependability of the measuring value obtained.

Control Unit

Figure 2:
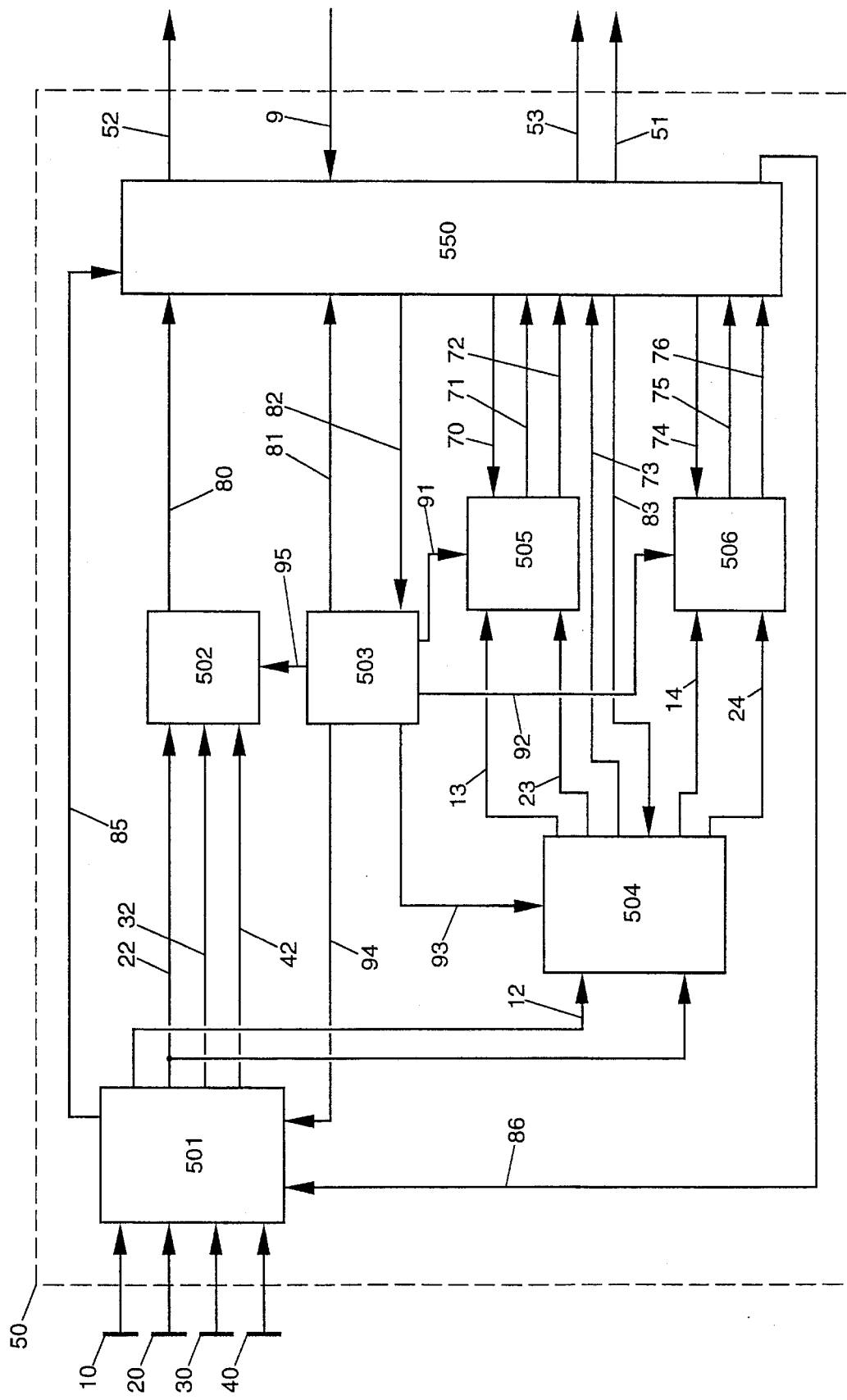
FIG. 2 is a block diagram representation of an evaluation apparatus according to the invention.

FIG. 2 is a block diagram of the control unit 50. The signals supplied by detectors 10, 20, 30 and 40 are supplied to a filtering and amplifying circuit 501. The filtering and amplifying circuit 501 conditions these signals to a uniform signal level and removes undesired high-frequency signal components.

The signal supplied from the detector 10 is processed by the amplifier-and-filter circuit 501 and passed, via a line 12, to an evaluating and correcting circuit 504. The signal supplied from the detector 20 is processed by the amplifier-and-filter circuit 501 and passed, via a line 22, to the evaluation and correction circuit 504 and also to a laser stabilization circuit 502. The signal supplied from the detector 30 is processed by the amplifier-and-filter circuit 501 and passed, via a line 32, to the laser stabilization circuit 502. The signal supplied by detector 40 is processed by the amplifier-and-filter circuit 501 and passed to the laser stabilization circuit 502 via a line 42.

The amplifier-and-filter circuit 501 supplies a signal indicative of its current set values for amplification to a system control 550 via a line 85. The amplifier-and-filtering circuit 501 also receives control signals from the system control 550 to alter the setting parameters of the amplifier-and-filter circuit 501.

The laser stabilization circuit 502 receives input signals on lines 22, 32 and 42 and provides an output signal on a line 80, which contains information for laser stabilization. The signal on line 80 is supplied to the system control 550. In response, the system control 550 provides the control signal on line 52 to drive the laser 1.

The evaluating and correcting circuit 504 evaluates the signals received on lines 12 and 22 for their correctness and, if need be, corrects them. If the laser is tuned to emit light of more than two wavelengths, the evaluating and correcting circuit 504 subdivides the signals on lines 12 and 22 into several signal pairs on lines 13 and 23 and 14 and 24, respectively, to provide two signal pulses within a signal period. The system control 550 provides a control signal over a line 83 to activate or deactivate the evaluating and correcting circuit 504. The evaluating and correcting circuit 504 provides a signal, via a line 73, to the system control 550 indicative of the degree of correction to the signals on lines 12 and 22. In this way, at least one signal pair is generated for every characteristic wavelength. In the described case, two signal pairs are generated.

The signals on lines 13 and 14 are derived from the signal on line 12. The signals on lines 23 and 24 are derived from the signal on line 22. The signal on line 13 is derived in such manner that the signal pulse that was generated by the light pulse with the uncharacteristic light wavelength in the detector 10 and the signal pulse which was generated by the light pulse with the light wavelength characteristic for the substance in the path 7 is contained in the signal 13. The signal on line 14 is derived from the signal 12 in such manner that the signal pulse that was generated by the uncharacteristic light wavelength in the detector 10 and the signal pulse that was derived by the light pulse with the light wavelength characteristic for the substance in the path 8 is contained in the signal on line 14. The signal on line 23 is derived from the signal on line 22 in such manner that the signal pulse that was generated by the light pulse with the uncharacteristic light wavelength in the detector 20 and the signal pulse that was generated by the light pulse with the light wavelength characteristic for the substance in the path 7 in the detector 20 is contained in the signal on line 23. The signal on line 24 is derived from the signal on line 22 in such manner that the signal pulse that was generated by the uncharacteristic light wavelength in the detector 20 and the signal pulse that was generated by the light pulse with the light wavelength characteristic for the substance in path 8 is contained in the signal on line 24.

The individual signal pulses are extended in their time course with the subdivision into different signals. The signal pulse in the signals on lines 13, 23, 14 and 24 which arises by reason of the light pulse with the uncharacteristic light wavelength is extended in such manner that it lasts exactly from the beginning of the signal period to its middle. The respective signal pulse in the signals on lines 13, 23, 14 and 24, which appears by reason of a light pulse with a characteristic light wavelength, is extended in such manner and its initial time point is displaced in such manner that it lasts from the middle of the signal period until the end of the signal period.

The signal on lines 13 and 23 are passed from the evaluating and correcting circuit 504 to a measurement value formation and correction circuit 505. Similarly, the signals on lines 14 and 24 are passed from the evaluating and correcting circuit 504 to the measurement value formation and correction circuit 506. The measurement value formation and correction circuit 505 receives signals on a line 70 from the system control 550 indicative of information for measurement value correction. Similarly, the measurement value formation and correction circuit 506 receives a signal on a line 74 from the system control 550 indicative of measurement value correction.

The measurement value formation and correction circuit 505 provides an output signal on a line 71 to the system control 550 indicative of the degree in which the output measurement value data provided on a line 72 was corrected. The measurement value and correction circuit 506 provides a signal to the system control 550 on a line 75 indicative of the degree in which the output measurement value data provided on a line 76 was corrected. The function and operation of the measurement value formation and correction circuits 505, 506 are described in greater detail with respect to FIGS. 7 and 8.

The system control 550 provides control signals to a beat signal generator 503 over a line 82 concerning information about the parameters of the system. The beat signal generator 503 provides a signal on a line 81 indicative of the system beat signal to the system control for synchronization. The beat signal generator 503 also provides system beat signals on lines 91, 92, 93, 94, and 95 to the measurement value formation and correction circuit 505, the measurement value formation and correction circuit 506, the evaluation and correction circuitry 504, the amplifier circuitry 501, and the laser stabilization circuitry 502, respectively, for synchronization.

Amplifier-and-Filter Circuitry

Figure 3:
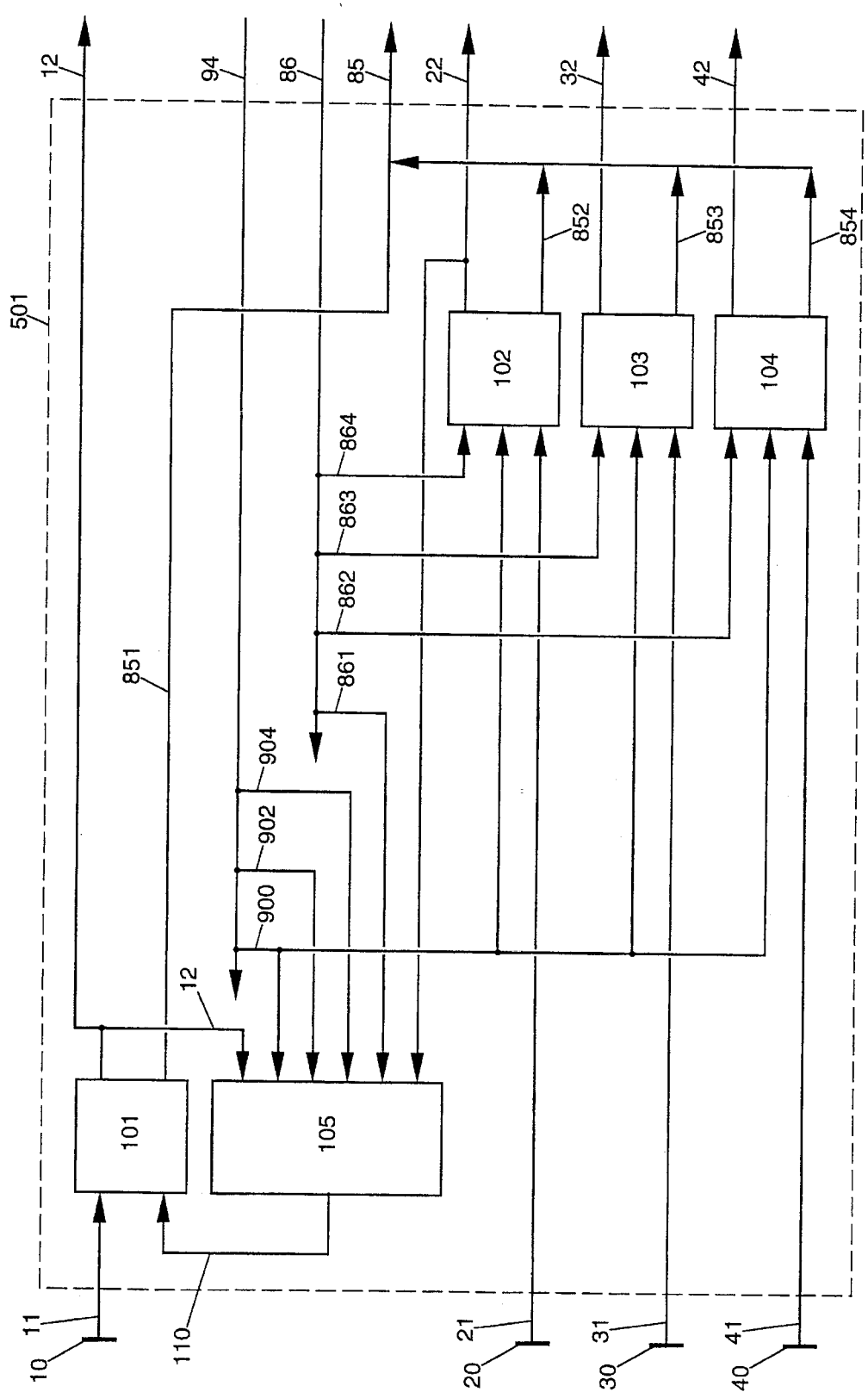
FIG. 3 is a block diagram representation of the filtering and amplification circuit used in the apparatus in FIG. 2.

FIG. 3 shows a block diagram of the amplifier-and-filter circuit 501 generally described above. The detect signal on line 11 is provided to an amplifier and filter 101. The detect signal on line 21 is provided to an amplifier and filter 102. The signal on line 31 is provided to amplifier and filter 103. The signal on line 41 is provided to an amplifier and filter 104.

The amplifier and filter 101 provides an output signal on line 12 obtained by amplification and filtering of the signal on line 11. The output signal on line 22 of the amplifier and filter 102 is obtained by amplification and filtering of the signal on line 21. The output signal on line 32 of the amplifier and filter 103 is obtained by amplification and filtering of the signal on line 11. The output signal on line 42 of the amplifier 104 is obtained by amplification and filtering of the signal on line 41.

The beat signal on a line 900 is obtained from the system beat signal on line 94 and is provided to the amplifier and filter 102. The beat signal on line 900 is likewise obtained from the system beat signal on line 94 and provided to the amplifier and filter 103. The beat signal on line 900 is provided to filter and amplifier 104.

All the filters in the amplifier-and-filter circuits 101, 102, 103 and 104 are set on the same limit frequency, and are preferably low-pass filters. Their limit frequency is preferably set in such a way that a signal with the same frequency that corresponds to the light pulse repetition rate is not altered. In other words, the limit frequency of the filters corresponds to the pulse repetition frequency in the detector signals on lines 11, 21, 31 and 41.

The amplifiers in the amplifier-and-filter circuits 102, 103 and 104 have their gain adjusted automatically so that the levels of the output signals on lines 22, 32 and 42 are approximately the same. The time constant of the regulating feedback loops is preferably set in such a way that to prevent oscillations of the regulating loop and consequently undesired components in the output signals on lines 22, 32 and 42. Any change in the gain of the amplifier-and-filter circuits 102, 103 and 104 occurs preferably synchronously to the beat signal on line 900 at the beginning of each new signal period. The signal evaluation in the electronic unit occurs only within one signal period to prevent a direct influence on the measurement value.

The gain of the amplifier and filter 101 is provided by a signal on line 110 by amplification adjustment circuitry 105. For the determination of the gain or amplification factor, the amplification adjustment circuitry 105 receives the output signal on line 12 from the amplifier and filter 101. The amplification adjustment circuitry 105 also receives beat signals on a lines 900, 902, 904 derived from the system beat signal. A signal for setting of the amplifier and filter parameters is provided to the amplification adjustment circuitry 105 on a line 861 which is obtained from the control signal on line 86. The output on line signal 22 of the amplifier and filter circuit 102 is also provided to the amplification adjustment circuitry 105.

The amplification adjustment circuitry 105 sets the level of output the signal on line 12 so that the signal level in the interval between the time point 730 and the time point 732 (FIG. 23) of the output signals on lines 12 and 22 is equal. If a level difference arises between these signals in the interval, then the new amplification factor is calculated from the level difference and set at the time point 730. In this way, any influence on the measurement result is avoided through the synchronous amplification adjustment at the start of a signal period.

The signal on line 861 permits automatic amplification regulation to be switched off and the amplification factor set manually. The amplifier and filter 102 also receives a signal on line 864 indicative of amplifier and filter parameters. This signal permits automatic amplification regulation of the amplifier and filter 102 to be switched off and the amplification factor set manually. The amplifier and filter circuit 103 also receives a signal on line 864 indicative of amplifier and filter parameters to permit the automatic amplification regulation of the amplifier and filter 103 to be switched off and the amplification factor set manually. Similarly, the amplifier and filter 104 receives a signal on line 862 indicative of the amplifier and filter parameters to permit the automatic amplification regulation of the amplifier and filter 104 to be switched off and the amplification factor assigned manually.

Laser Stabilization

Figure 4:
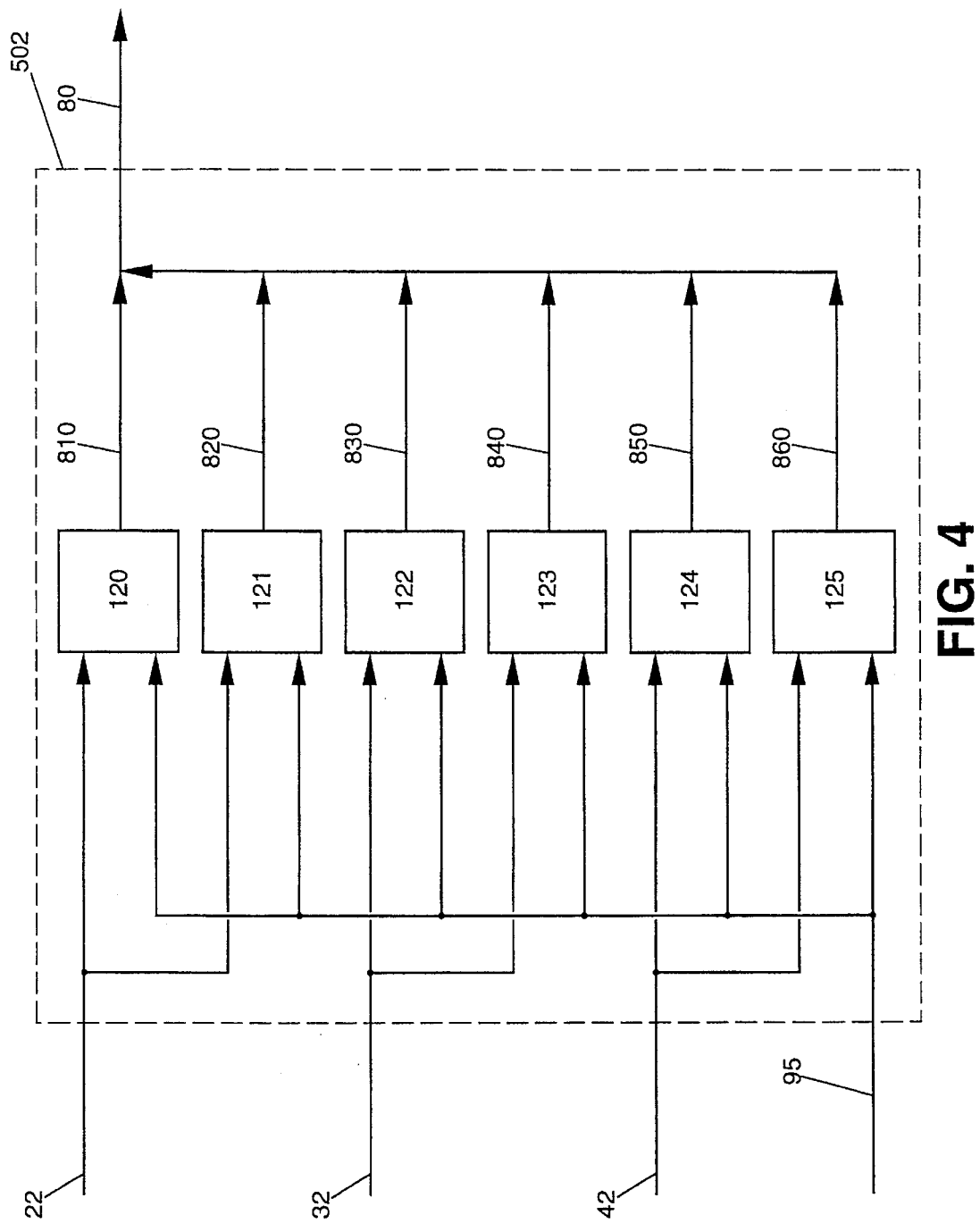
FIG. 4 is a block diagram representation of the signal processing circuitry for laser stabilization of the apparatus in FIG. 2.

FIG. 4 shows a block diagram of the laser stabilization circuitry 502 for signal conditioning. As noted above, the signal on line 22 is the conditioned signal provided from the detector 20. The signal on line 32 is the conditioned signal provided from the detector 30. The signal on line 42 is the conditioned signal provided from the detector 40. The signal on line 95 is the system beat signal.

The signal on line 22 is supplied to sample-and-hold circuit 120 and a rectifier circuit 121. The signal on line 32 is supplied to a sample-and-hold circuit 122 and a rectifier circuit 123. The signal on line 42 is provided to a sample-and-hold circuit 124 and a rectifier circuit 125. The system beat signal on line 95 is provided to the sample-and-hold circuit 120, the rectifier circuit 121, the sample-and-hold circuit 122, the sample-and-hold circuit 123, the sample-and-hold circuit 124, as well as the rectifier circuit 125.

The sample-and-hold circuit 120 provides an output signal on a line 810 that forms a portion of a laser status signal on line 80. The rectifier circuit 121 also provides an output signal at line 820 that forms the laser status signal at line 80. The sample-and-hold circuit 122 similarly provides an output signal at line 830 that forms the laser status signal at line 80. The rectifier circuit 123 also provides an output signal at line 840 that forms a portion of the laser status signal at line 80. The sample-and-hold circuit 124 also provides a signal at line 850 forming a portion of the laser status signal 80. Likewise, the rectifier circuit 125 provides an output signal at line 860 that forms a portion of the laser status signal at line 80.

The sample-and-hold circuit 120 samples the signal received on line 22 at time points provided by the system beat signal on line 95. Similarly, the sample-and-hold circuit 122 samples the signal received on line 32 at time points given by the system beat signal on line 95. The sample-and-hold circuit 124 also samples the signal on line 42 at time points provided by the system beat signal on line 95.

The rectifier circuit 121 determines, within an interval provided by the system beat signal, the maximal value and the average value of the signal received on line 22. The rectifier circuit 123 determines, within an interval provided by the system beat signal, the maximal value and the average value in the signal on line 32. The rectifier circuit 125 determines, within an interval provided by the system beat signal, the maximal value and the average value in the signal provided on line 42.

Beat Generator Circuitry

Figure 5:
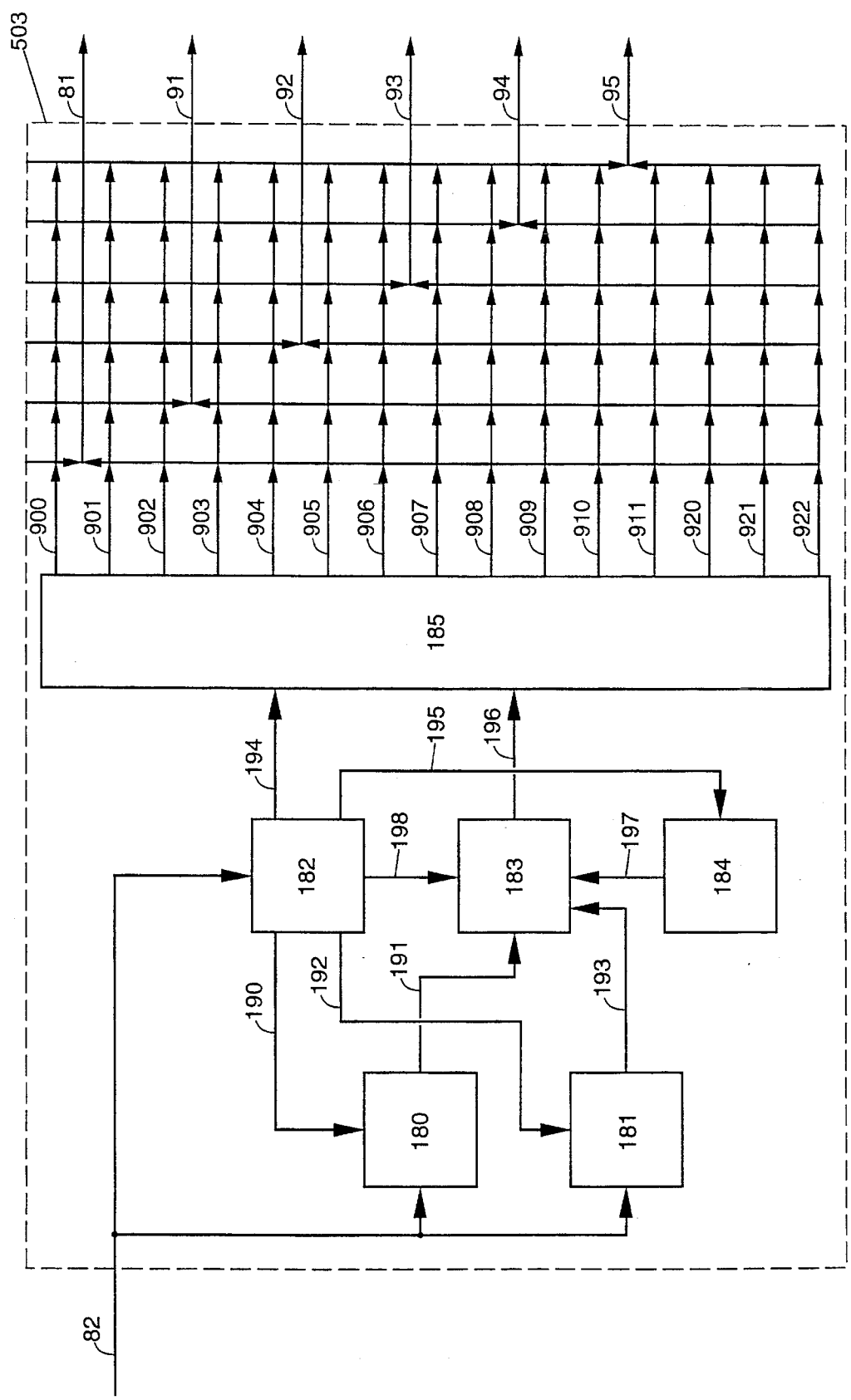
FIG. 5 is a block diagram representation of the pulse generator circuitry in FIG. 2.

FIG. 5 shows the beat signal generator 503 in greater detail. The signal on line 82 is provided to data control circuitry 182 and to a data register 180. The beat information signal on line 82 is also provided to an address register 181. The system control 550 supplies and receives data from a beat pattern data storage unit 183 via signals supplied on line 82 to the control circuitry 182.

The control circuitry 182 supplies signals to the data register 180 on a line 190. The control circuitry 182 also provides signals to the address register 181 on a line 192. The signal on lines 190 and 192 control the data register 180 and the address register 181 to permit data exchange between the data storage unit 183 and the system control without interrupting the output of the beat signal pattern on a line 196.

The control circuitry 182 supplies signals on a line 198 to the data storage unit 183. The control circuitry 182 also supplies signals to the address generator 184 over a line 195. In addition, the control circuitry 182 provides signals on a line 194 to the output register 185. The data storage unit 183 supplies data signals to the output register 185 via a line 196.

The output register 185 provides output beat or pulse signals at lines 900, 901, 902, 903, 904, 905, 906, 907, 908, 909, 910, 911, 920, 921, and 922, each of which are available at a given time.

The beat signals at lines 900, 901, 902, 903, 904, 905, 906, 907, 908, 909, 910, 911, 920, 921 and 922 are combined as shown in FIG. 5 into a first system beat signal on line 81. The beat signals 900, 901, 902, 903, 904, 905, 906, 907, 908, 909, 910, 911, 920, 921 and 922 are also combined (as shown in FIG. 5) into a second system beat signal on line 91. The beat signals 900, 901, 902, 903, 904, 905, 906, 907, 908, 909, 910, 911, 920, 921 and 922 are combined as shown in FIG. 5 into a third system beat signal on line 92. The beat signals 900, 901, 902, 903, 904, 905, 906, 907, 908, 909, 910, 911, 920, 921 and 922 are combined as shown in FIG. 5 into a fourth system beat signal on line 93. The beat signals 900, 901, 902, 903, 904, 905, 906, 907, 908, 909, 910, 911, 920, 921 and 922 are also combined as shown in FIG. 5 into a fifth system beat signal on line 94. The beat signals 900, 901, 902, 903, 904, 905, 906, 907, 908, 909, 910, 911, 920, 921 and 922 are also combined as shown in FIG. 5 into a sixth system beat signal on line 95.

The data control circuitry 182 coordinates the runoff between the address generator 184, the data storage unit 183 and the output register 185 in such manner that a continuous data flow is supplied to the output register 185 as will be understood by those skilled in the art. The output register 185 regularly receives data on line 196 to provide the desired output beat pattern data at lines 900, 901, 902, 903, 904, 905, 906, 907, 908, 909, 910, 911, 920, 921 and 922.

The system control supplies the beat information signal on line 82 to the data storage unit 182 as follows. The beat signal on line 900 indicates the beginning of a new signal period and the end of the second characteristic signal pulse in signals on lines 12, 22, 32 and 42. The beat signal 901 indicates the end of the first quarter of the uncharacteristic signal pulse in the signals on lines 12, 22, 32 and 42. The beat signal 902 indicates the end of the first half of the uncharacteristic signal pulse in the signals on lines 12, 22, 32 and 42. The beat signal 903 indicates the end of the third quarter of the uncharacteristic signal pulse in the signals on lines 12, 22, 32 and 42. The beat signal 904 indicates the end of the uncharacteristic signal pulse and the beginning of the first characteristic signal pulse in the signals on lines 12, 22, 32 and 42. The beat signal 905 indicates the end of the first quarter of the first characteristic signal pulse in the signals on lines 12, 22, 32 and 42. The beat signal 906 indicates the end of the first half of the first characteristic signal pulse in the signals on lines 12, 22, 32 and 42. The beat signal 907 indicates the end of the third quarter of the first characteristic signal pulse in the signals on lines 12, 22, 32 and 42. The beat signal 908 indicates the end of the first characteristic signal pulse and the beginning of the second characteristic signal pulses in the signals on lines 12, 22, 32 and 42. The beat signal 909 indicates the end of the first quarter of the second characteristic signal pulse in the signals on lines 12, 22, 32 and 42. The beat signal 910 indicates the end of the first half of the second characteristic signal pulse in the signals on lines 12, 22, 32 and 42. The beat signal 911 indicates the end of the third quarter of the second characteristic signal pulse in the signals on lines 12, 22, 32 and 42.

The beat signal 920 indicates the beginning of the signal period for the measurement value formation. The beat signal 921 indicates the middle of the uncharacteristic signal pulse for the measurement value formation. The beat signal 922 indicates the middle of the characteristic signal pulse for the measurement value formation.

Signal Evaluation And Correction Circuitry

Figure 6:
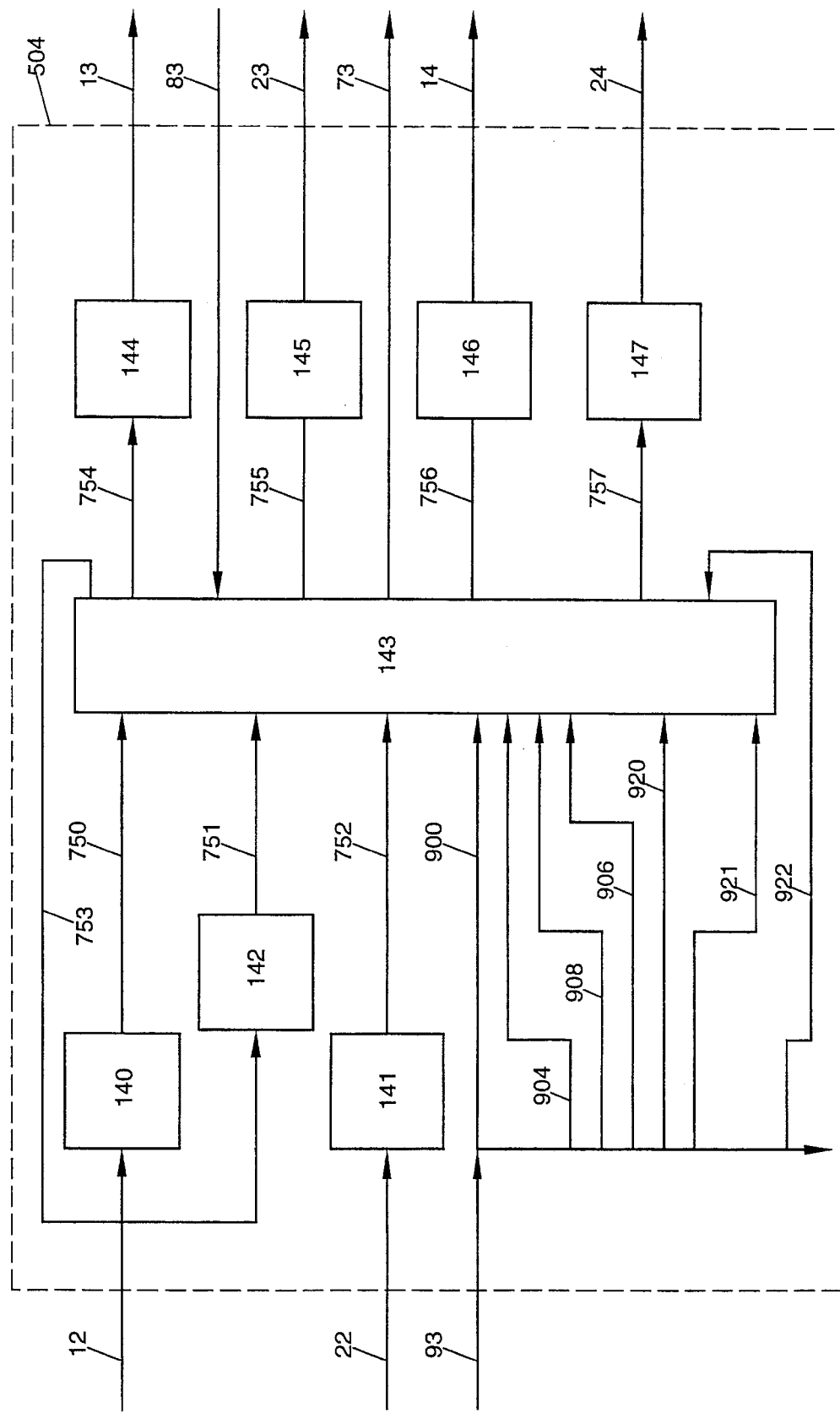
FIG. 6 is a block diagram representation of the evaluating and correcting circuitry in FIG. 2.

FIG. 6 shows the evaluation and correction circuitry 504 in greater detail. The input signal on line 12 is provided to an analog/digital converter 140. The input signal on line 22 is provided to an analog/digital converter 141. The analog/digital converter 140 transforms the received analog signal into a digital signal on line 750. The information content of the signals on line 12 and 750 is the same. The analog/digital converter 141 transforms the received analog signal into a digital signal on line 752. The information content of the signals on lines 22 and 752 is the same.

The output digital signal of the analog/digital converter 140 is provided on line 750 to evaluation and correction circuitry denoted by a block 143. The output digital signal of the analog/digital converter 141 is likewise provided on line 752 to the evaluation and correction circuitry 143.

A desired-value storage unit 142 receives data indicative of desired values from the evaluation and correction circuitry 143 on a line 753. The evaluation and correction circuitry 143 reads desired value data from the desired value storage unit 142 on a line 751.

The evaluation and correction circuitry 143 provides an output signal on a line 754 to a digital/analog converter 144. The digital/analog converter 144 transforms the digital signal on line 754 into the analog signal on line 13. The information content of the signals on lines 754 and 13 is the same. The evaluation and correction circuitry 143 also provides an output signal on a line 755 to a digital/analog converter 145. The digital/analog converter 145 transforms the digital signal into the analog signal on line 23. The information content of the signals on lines 755 and 23 is the same. The evaluation and correction circuitry 143 also provides an output signal on a line 756 to digital/analog converter 146. The digital/analog converter 146 transforms the digital signal on line 756 into an analog signal on line 14. The information content of the signals on lines 756 and 14 is the same. The evaluation and correction circuitry 143 also provides an output signal on a line 757 to digital/analog converter 147. The digital/analog converter transforms the digital signal on line 757 into an analog signal on line 24. The information content of the signals on lines 757 and 24 is the same.

From the system beat signal on line 93, a beat signal on line 900 is provided to the evaluation and correction circuitry 143. A beat signal on line 904 is also derived from the system beat signal and provided to the evaluation and correction circuitry 143. The beat signals on lines 906, 908, 920, 921, and 922 are also derived from the system beat signal on line 93 and provided to the evaluation and correction circuitry 143. The beat signals on lines 900, 904, 906 and 908 synchronize the evaluation and correction circuitry 143 with the input signals on lines 12 and 13 and 750 and 752, respectively. The beat signals 920, 921 and 922 synchronize the output signals 754, 755, 756 and 757 of the evaluation and correction circuitry 143.

The beat signal on line 900 indicates the start of a signal period and the end of the second characteristic signal pulse in the signals on lines 12 and 22. The beat signal on lines 904 indicates the end of the uncharacteristic signal pulse in the signals on lines 12 and 22. The beat signal on lines 906 indicates the middle of the signal period in the signals on lines 12 and 22. The beat signal on line 908 indicates the end of the first characteristic signal pulse in the signals on lines 12 and 22. The beat signal on line 920 indicates the beginning of the signal period of the output signals on lines 754, 755, 756 and 757. The beat signal on line 921 indicates the middle of the first pulse in the output signals on lines 754, 755, 756 and 757. The beat signal on line 922 indicates the middle of the second pulse in the output signals on lines 754, 755, 756 and 757.

The evaluation and correction circuitry 143 reads-in the data flow on line 750 and the data flow on line 752 within a signal period and temporarily stores both data flows. After the data of a period is read-in, the data of the next signal period are read into another storage unit.

Simultaneously with the reading-in of the data of the next signal period, the data of the preceding signal period are evaluated. The six intermediately-stored signal pulses are normalized for the evaluation. Six normalizing factors are temporarily stored for this purpose. Thereafter, the three signal pulses from the signal on line 22 are compared with the desired values stored in the desired-value storage unit 142. If the pulses deviate from the stored values, the pulses are correspondingly corrected. The three signal pulses in the signal on line 22 must always correspond to the stored values in the desired-value storage unit 142. For the further evaluation of the temporarily stored signal pulses, their first derivative is calculated and likewise compared with stored data corresponding to the first derivatives located the desired-value storage unit 142 and, if need be, corrected.

Since the light beam 200 of the laser 1 passes directly over the beam dividers 2 and 3 to the detector 20, the signal on line 22 contains only disturbances that were caused by the system itself. The same disturbances are also contained in the signal on line 12. The same corrections made to the signal pulses of the signal on line 22 are applied to the signal pulses of the signal on line 12. After the correction, the signal pulses of the signal on line 12 are compared with the desired values from the desired-value storage unit 142. Since the individual pulses were normalized, the effect of the absorption of the light beam on the measuring interval, however, leads to no deformation of the individual light pulses. Any pulse alterations are due to other causes. The normalized pulse can be corrected, therefore, without negative effect on the measurement value formation. After the evaluation and correction, the individual pulses with the temporarily stored normalization factors are reconverted to their original amplitude. Alternatively, the stored curve data can be recalculated to the current amplitude.

The data on lines 750 and 752 are then subdivided into the data flows on lines 754, 755, 756 and 757. Each of the two data flows on lines 750 and 752 comprises the data of the uncharacteristic light pulse and two characteristic light pulses. The data flow on line 750 is subdivided to provide data flows on lines 754 and 756. The data flow on line 756 contains the data of the uncharacteristic signal pulse and the data of the second characteristic signal pulse. The data flow on line 752 is also subdivided to data flows on lines 755 and 757. The data flow on line 755 contains data of the uncharacteristic signal pulse and the data of the first characteristic signal pulse. The data flow on line 757 contains data of the uncharacteristic signal pulse and the data of the second characteristic signal pulse.

This subdivision of the data flows on lines 750 and 752 simultaneously shifts the timing and the phase position of the individual pulses. The uncharacteristic signal pulse is shifted so that it begins at the start of the signal period and ends in the middle of the signal period. The characteristic signal pulse is shifted so that it begins in the middle of the signal period and ends at the end of the signal period. The output of the data flows on lines 754, 755, 756 and 757 is now synchronized with the beat signals 920, 921 and 922.

Measurement Value Formation Circuitry

Figure 7:
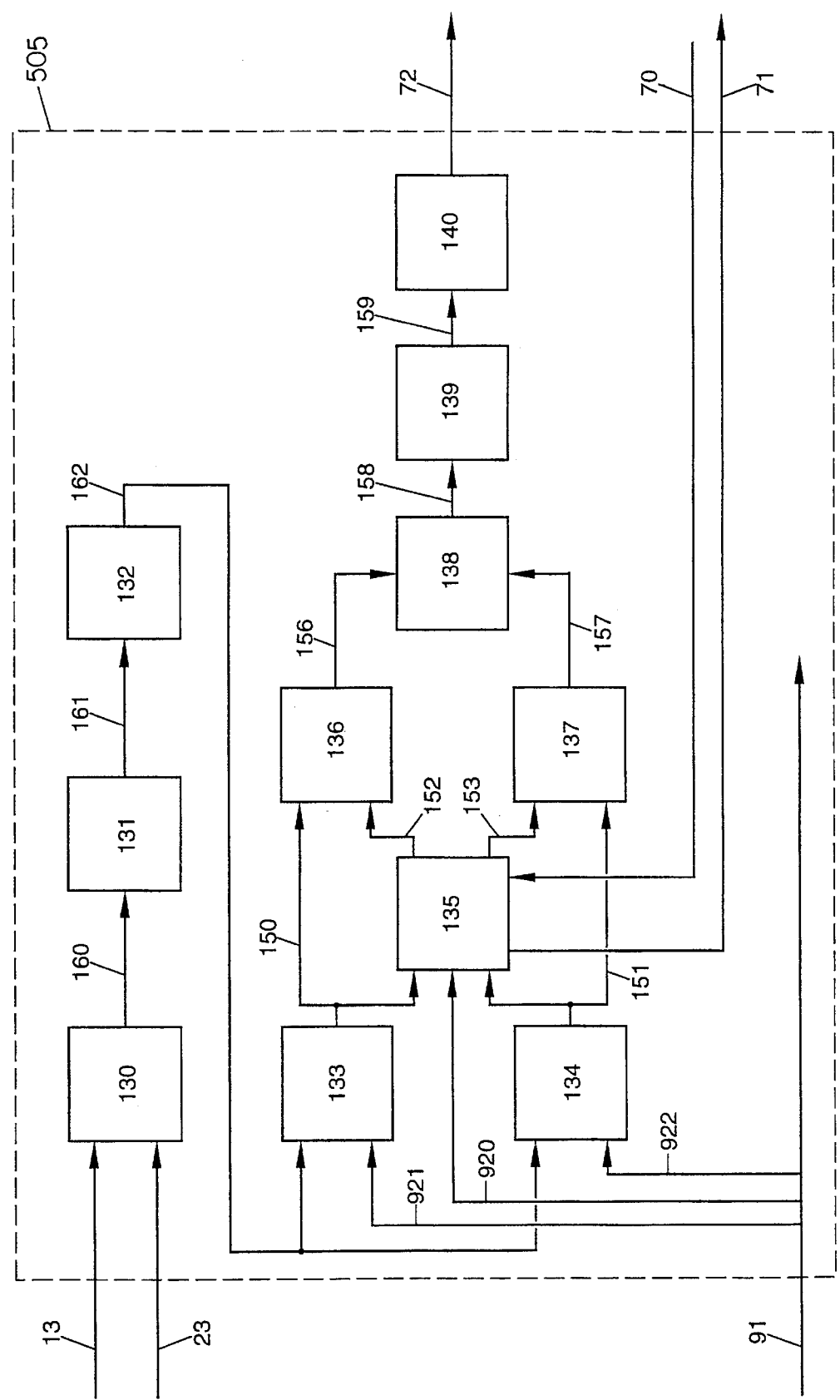
FIG. 7 is a block diagram representation of the measurement-value forming and correcting circuitry in FIG. 2.

The measurement value formation and correction circuitry 505 is shown in FIG. 7. The signal on line 13 is provided to a subtractor circuit 130. The subtractor circuit 130 also receives the signal on line 23 and provides the difference between the signals on a line 160.

Fundamentally, the chosen polarity of the output signal on line 160 of the subtractor circuit 130 plays no role in the present invention; however, to simplify the representation, a positive signal 160 is described in the following description denoting the presence of a sought-out gas on the measuring path 5 and the evaluating electronic system correctly calibrated.

The output signal on line 160 is provided to an amplifier 131. The output signal on line 161 of the amplifier 131 is passed to a filter 132. The filter is preferably a low-pass filter which filters the signal from undesired frequency components. Its limit frequency corresponds to at least half the pulse repetition frequency of the signals on lines 13 and 23. The gain of the amplifier 131 can be adjusted by the system control 550 with appropriate modification. A suitable sample-and-hold circuit may also be interposed between the subtractor and filter to sample the output signal of the subtractor only when a difference has been established.

The signal on line 13 is derived from the electrical signal of the detector 10 disposed proximate the measuring path 5. The signal on line 23 is derived from the electrical signal of the detector 20 disposed proximate the reference path 6. The signals on lines 13 and 23 are balanced so that their amplitude during the emission of the uncharacteristic light pulse through the laser 1 is the same. The output signal of the subtractor 130 is therefore zero during the emission phase. Since the two signals on lines 13 and 23 are derived from the same light beam 200, changes, for example in the intensity of the light beam, provide no signal difference on the output of the subtractor 130. Accordingly, no interferences of the light beam 20 caused by the laser and its drive are present in the signal on line 160. On the other hand, if the laser 1 emits light with a characteristic wavelength, the signal on line 13, in dependence on the concentration of the investigated gas, will have a lower amplitude than the signal on line 23. The gas under investigation will damp the light beam 203 on the measuring path 5 at the characteristic wavelength proportionally to its concentration. Since the investigated gas is not present on the reference path 6, the light beam 204 is not damped. The amplitude of the output signal 160 of the subtractor 130 will rise consequently during the emission of the light beam 200 with the characteristic light wavelength proportionally to the concentration of the investigated gas on the measuring interval.

The output signal on line 162 is provided to sample-and-hold circuits 133 and 134. The beat signal on line 921 (derived from the system beat signal on line 91) is provided to the sample-and-hold circuit 133. The beat signal on line 921 indicates the middle of the uncharacteristic signal pulse. The sample-and-hold circuit 133, therefore, samples the difference signal on line 162 exactly in the middle of the uncharacteristic signal pulse. The beat signal 922 (also derived from the system beat signal on line 91) is provided to the sample-and-hold circuit 134 on line 922. The beat signal on line 922 indicates the middle of the characteristic light pulse. The sample-and-hold circuit 134, therefore, samples the signal on line 162 exactly in the middle of the characteristic signal pulse.

The output signal on line 150 of the sample-and-hold circuit 133 is provided to sample-and-hold circuit 136 and to a tolerance assessment circuit 135. The output signal on line 151 of sample-and-hold circuit 134 is provided to the sample-and-hold circuit 137 and to the tolerance assessment circuit 135. The beat signal on line 920 (derived from system beat signal on line 91) is provided to the tolerance assessment circuit 135. The tolerance assessment circuit 135 also receives control signals on line 70 from the system control 550. The tolerance assessment circuit 135 also provides signals on a line 71 to the system control 550. The signals on line 70 are indicative of the permissible absolute values of the signals on lines 150 and 151 as well as the permissible changes in the signals on lines 150 and 151. The signal on line 71 is indicative of the degree in which the signals on lines 150 and 151 are inhibited.

The tolerance assessment circuitry 135 provides a control signal on line 152 to acquire the data on line 150 from the sample-and-hold circuit 136 at the end of a signal period. The tolerance assessment circuit 135 provides a signal on line 153 to acquire data on line 151 from the sample-and-hold circuit 137 at the end of a signal period.

The sample-and-hold circuit 136 also provides an output signal on a line 156 to the subtractor 138. The sample-and-hold circuit 137 likewise provides an output signal on a line 157 to the subtractor 138. The subtractor 138 provides the difference between the signals on lines 136 and 137. This signal is the difference in the signal amplitude of the signal on line 162 during the middle of the characteristic signal pulse and the middle of the uncharacteristic signal pulse. The output signal on line 158, therefore, is a measure for the concentration of the investigated gas on the measuring interval 5.

The output signal on line 158 is provided to an amplifier 139. The amplifier 139 provides an output signal on line 159 to the filter 140. The function of filter 140 is primarily for smoothing the signal since changes in the concentration of the investigated gas on the measuring interval 5 are detected as stepwise changes by reason of the behavior of the sample-and-hold circuits 133, 134, 136 and 137. The filter 140 provides an output signal on line 72 to the system control for further processing.

Measurement Value Formation For
Cross-Sensitivity Correction

Figure 8:
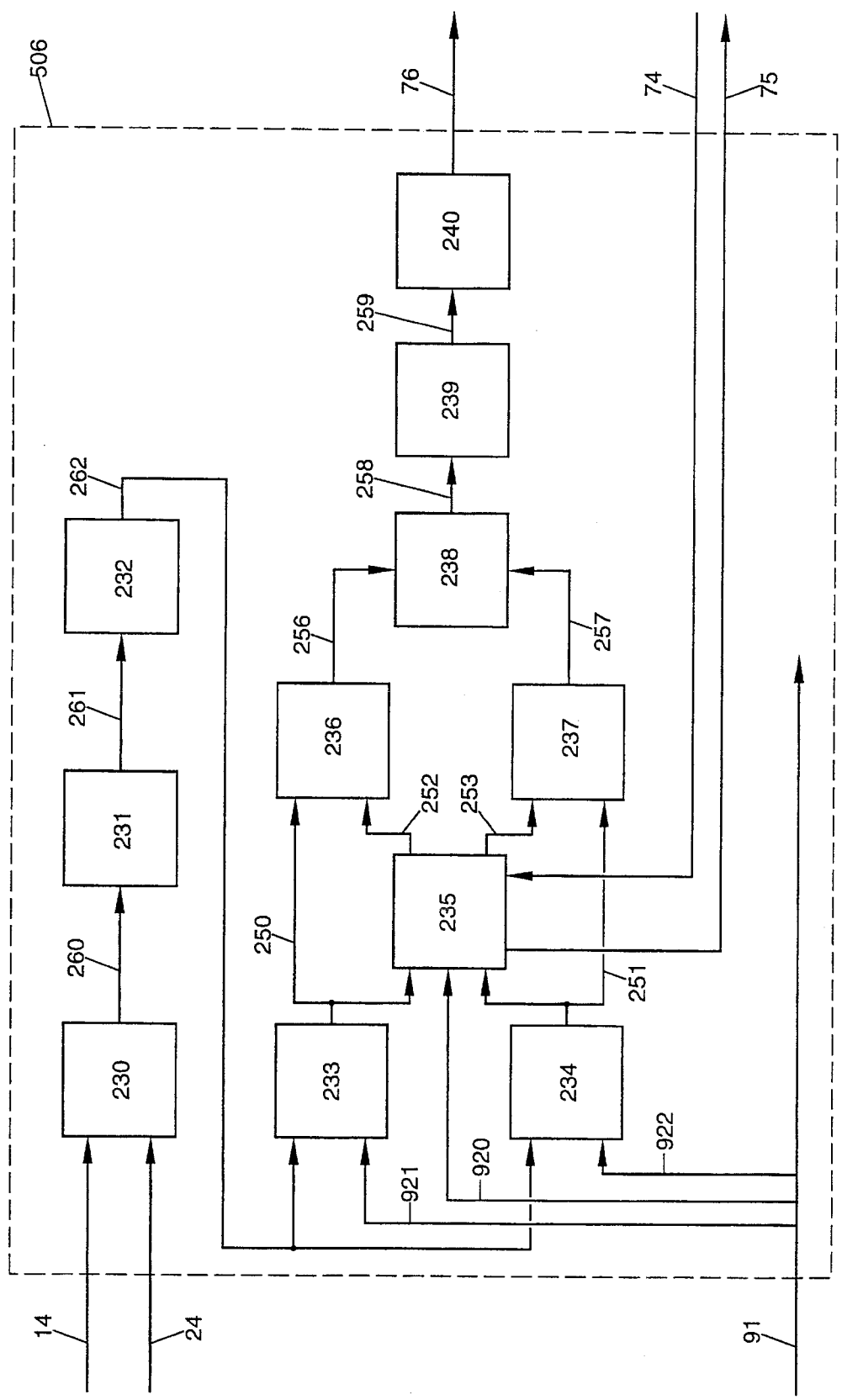
FIG. 8 is a block diagram representation of the measurement-value forming and correcting circuitry of FIG. 7 for providing cross-sensitivity correction.

The measurement value formation and cross-sensitivity correction denoted by a block 506 is represented in FIG. 8. As shown therein, the signals on lines 14 and 24 are provided to subtractor 230. The subtracter 230 provides the difference between these signals at a line 260. The chosen polarity of the output signal on line 260 is likewise described as positive for ease of explanation.

The output signal on line 260 is provided to an amplifier 231. The amplifier 231 provides an output signal on line 261 to filter 232. The filter is preferably a low-pass filter with a limit frequency fitted to the dynamics of the total system. Its limit frequency corresponds to at least half the pulse-repetition frequency of the signals on lines 14 and 24. The gain of the amplifier 231 can be made adjustable by the system control 550. As noted above, a sample-and-hold circuit may be interposed between the subtractor and amplifier.

The signal on line 14 is derived from the electrical signal of the detector 10 disposed proximate the measuring path 5. The signal on line 24 is derived from the electrical signal of the detector 20 disposed proximate the reference path 6. The signals on lines 14 and 24 are balanced in such a way that their amplitude is equal during the emission of the uncharacteristic light pulse through the laser 1. The output signal of the subtracter 230, therefore, is zero during this emission phase. Since the two signals 14 and 24 are derived from the same light beam 200, changes in the intensity of the light beam do not result in an output of the subtracter 230 varying from zero. Accordingly, there will not be any disturbances of the light beam 200 caused by the laser and its drive, in the difference signal at line 260. If the laser 1 emits light with a characteristic light wavelength, then the signal on line 14, dependent on the concentration of the investigated gas (which is the cause for the cross-sensitivity), will have a lower amplitude than the signal on line 24. The investigated gas (the cause of the cross-sensitivity) will damp the light beam 203 on the measuring path 5 at the characteristic wavelength in proportion to its concentration. Since the investigated gas is not present on the reference path 6, the light beam 204 is not damped. The amplitude of the output signal on line 260 will therefore rise during the emission of the light beam 200 with the characteristic light wavelength in proportion to the concentration of the investigated gas.

The filter 232 provides an output signal on line 262 to sample-and-hold circuits 233 and 234. Beat signal on line 921 (derived from system beat signal 91) is provided to the sample-and-hold circuit 233. The beat signal on line 921 is indicative of the middle of the uncharacteristic signal pulse. Upon receipt, the sample-and-hold circuit 233 samples the signal on line 262 exactly in the middle of the uncharacteristic signal pulse. A second beat signal on line 922 (derived from the system beat signal 91) is provided to sample-and-hold circuit 234. The beat signal on line 922 is indicative of the middle of the characteristic light pulse. Upon receipt, the sample-and-hold circuit 234 samples the signal on line 262 in the middle of the characteristic pulse.

The sample-and-hold circuit 233 provides an output signal on line 250 to sample-and-hold circuit 236 and to tolerance assessment circuit 235. The sample-and-hold circuit 234 provides an output signal on line 251 to sample-and-hold circuit 237 and to the tolerance assessment circuit 235. The beat signal 920 (derived from the system beat) is provided to the tolerance assessment circuit 235. The tolerance assessment circuit 235 also receives signals on a 74 from the system control 550. The tolerance assessment circuit 135 also provides signals on a line 75 to the system control 550. The system control 550 provides, via line 74, the admissible absolute values of the signals at lines 250 and 251 as well as the permissible changes in the signals 250 and 251. The tolerance evaluation circuitry 235 provides, via line 75, to the system control 550 the degree in which the signal(s) on lines 250 and 251 are inhibited.

The tolerance assessment 235 enables, via the signal on line 252, acquisition of the signal on line 250 by the sample-and-hold circuit at the end of a signal period. The tolerance assessment circuitry 235 enables, via the signal on line 253, the acquisition of the signal on line 251 by the sample-and-hold circuit 237 at the end of a signal period.

The sample-and-hold circuit 236 provides an output signal on a line 256 to subtracter 238. The sample-and-hold circuit 237 provides an output signal on line 257 to subtracter 238. The subtracter provides the difference between the signals on lines 236 and 237 at an output 258. This signal represents the difference in the signal amplitude of the signal at line 262 during the middle of the characteristic signal pulse and the middle of the uncharacteristic signal pulse. The output signal at line 258 is therefore a measure for the concentration of the selected gas (which is the cause of the cross-sensitivity) on the measuring path 5.

The subtracter 238 provides the signal at line 258 to amplifier 239. The output signal of the amplifier 239 is provided to filter 240 at line 259. The function of filter 240 is primarily the smoothing of the signal 259 since changes in the concentration of the selected gas on the measuring path 5, are detected as stepwise by reason of the sample-and-hold circuits 233, 234, 236 and 237. The filter 240 provides an output signal at line 72 to the system control for further processing.

Laser Stabilization, Part 1

During start-up, the laser source is controlled with any desired control signal. The control signal is adjusted until there is an adjusted signal level supplied to rectifier circuitry in the reference path. The sample-and-hold circuits sample the waveshape and the phase position of the signal in the reference path.

By moving the individual phase signals, the signal from the reference path may be evaluated. By moving the individual phase pulses the signal may be registered completely. If the signal from the reference path does not comprise three relative maxima, the laser control must be varied and the sampling must be repeated. If the signal alternatively comprises of four minima, it is evaluated to determine whether the maxima are each imbedded symmetrically between two minima. As long as these conditions are not met, the laser control signal is varied.

As soon as these conditions are met, sample-and-hold circuitry in the calibration paths samples the detected signals to determine whether the required light wavelengths are emitted by the laser and at what the time such light is emitted. If the laser is adjusted correctly, a signal pulse—caused by the light pulse with the uncharacteristic light wavelength—will appear unweakened in the two calibration paths. The two other signal pulses will be weakened in at least one path each. The light pulse, whose wavelength is characteristic for gas, and whose concentration is to be determined in the measuring path, will also be weakened in the second calibration path. The reason is the cross-sensitivity. The light pulse, whose wavelength is characteristic for the substance and represents the reason for the cross-sensitivity, may only be weakened when passing through that path which contains this substance. If the light rays are weakened in both characteristic light wavelengths when passing through the calibration path, the laser is adjusted incorrectly.

Emission wavelength and emission intervals of the radiation source are determined repeatedly by sampling the calibration signals with sample-and-hold circuitry, and corrected, if necessary. Because the phase position of the signals is identical in all paths, sampling the calibration signals at the interval when the maxima occur in the reference path, is sufficient. If this condition in the calibration paths is not met, the laser is adjusted until this is the case.

During operation the control signal of the laser is continuously varied. The changes must be kept small, so that an influence on the measured result is prevented, or else, this must be taken into account when the measured value is established. The sequence in which the various light wavelengths are emitted, may be changed. However, this must be taken into account when the signals are demultiplexed.

If the laser is adjusted to the various light wavelengths with a mechanically moved adjusting element, it is more favorable to permit the adjusting element to make a cyclical movement without sudden changes. If the adjusting element is moved back and forth with a steady movement between the two end points without sudden change, the emission spectrum is sampled once from the low to the high and once from the high to the low wavelength.

This has an undesired side-effect. If the light wavelengths to be used are not directly adjacent in the emission spectrum of the laser, the laser also emits on all emission lines which are in between. This must be taken into account during demultiplexing in the evaluation and correction equipment. In demultiplexing—the division into different signals of two signal pulses—, the undesired signal pulses are simply omitted.

There are multiple application examples where the advantages of the radiation source stabilization become clear. In addition to the application for spectroscopic concentration determination of substances with the aid of a stabilized radiation source—as described below—the invention may also be used for procedures to measure path lengths. With radiation, whose precise wavelength is know, the distance between two points may be accurately determined. For a reliable determination of path length it is essential to maintain the path length used. With the procedure described herein to stabilize radiation sources, the radiation source may also be adjusted cost-efficiently and without degradation to the desired wavelength which is determined by the substance in the calibration path.

Figure 9:
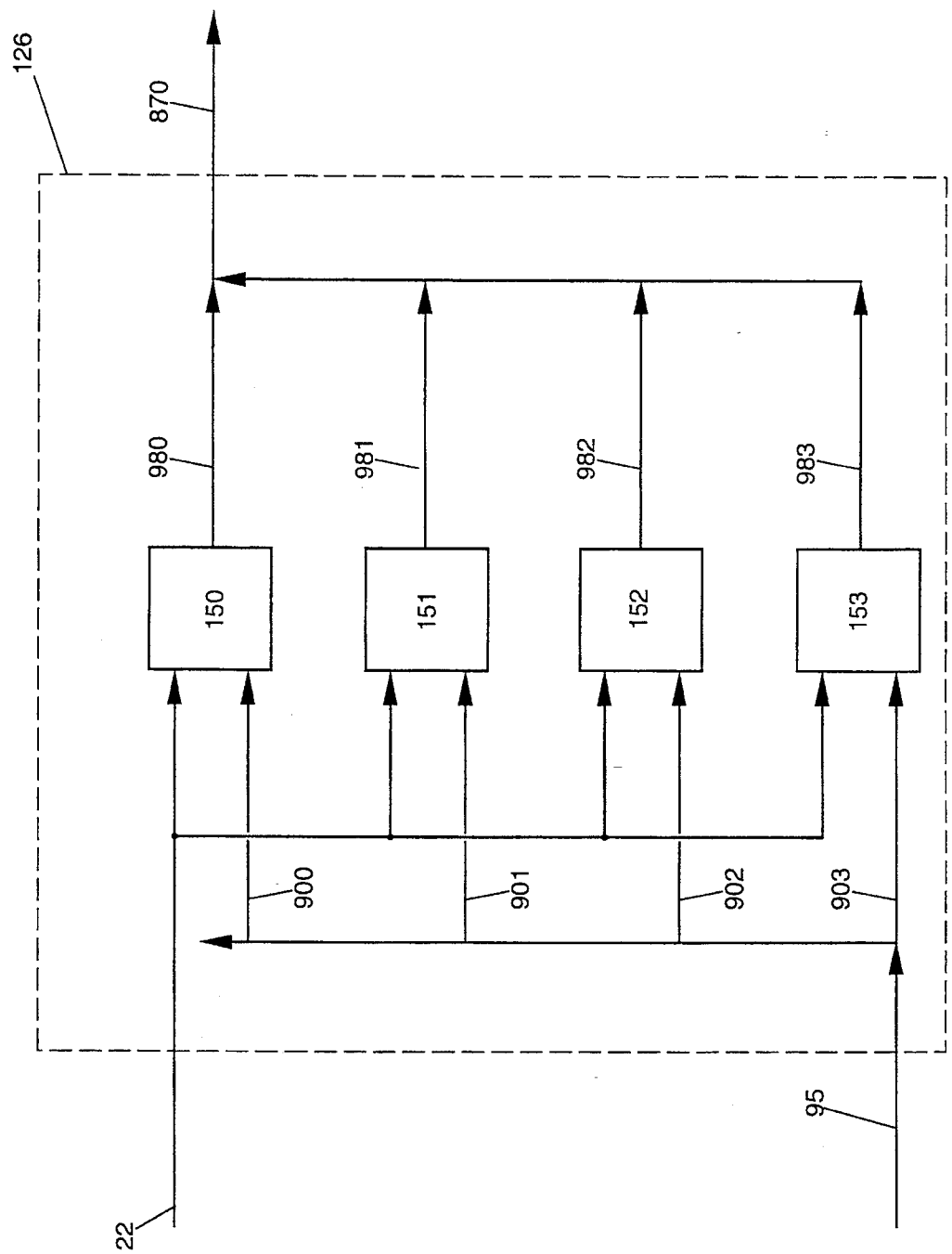
FIGS. 9–17 are block diagram representations of other circuits of the laser stabilization circuitry in FIG. 2.

FIG. 9 shows laser stabilization circuity which determines data of an uncharacteristic signal pulse. The signal on line 22 passed to sample-and-hold circuits 150, 151, 152 and 153. The beat signal on line 900 (derived from the system beat signal on line 95) is provided the sample-and-hold circuit 150. The beat signal on line 900 is indicative of the beginning of a signal period and the beginning of the uncharacteristic signal pulse. A beat signal on line 901 (derived from the system beat signal on line 95) provided to sample-and-hold circuit 151. The beat signal on line 901 is indicative of the end of the first quarter of the uncharacteristic signal pulse. A beat signal on line 902 (derived form the system beat signal in line 95) is provided to the sample-and-hold circuit 152. The beat signal on line 902 is indicative of the middle of the uncharacteristic signal pulse. A beat signal on line 903 (also derived from the system beat signal in line 95) is provided to the sample-and-hold circuit 153. The beat signal 903 is indicative of the end of the third quarter of the uncharacteristic signal pulse.

The sample-and-hold circuit 150 samples the signal on line 22 upon receipt of the signal on line 900. The sample-and-hold circuit 151 samples the signal on line 22 upon receipt of the signal on line 901. The sample-and-hold circuit 152 samples the signal on line 22 upon receipt of the signal on line 902. The sample-and-hold circuit 153 samples the signal on line 22 upon receipt of the signal on line 903.

The output signal on line 980 of the sample-and-hold circuit 150, the output signal on line 981 of sample-and-hold circuit 151, the output signal on line 982 of sample-and-hold circuit 152, and the output signal on line 983 of sample-and-hold circuit 153 are combined to form a combined output signal on line 870.

Laser Stabilization, Part 2

Figure 10:
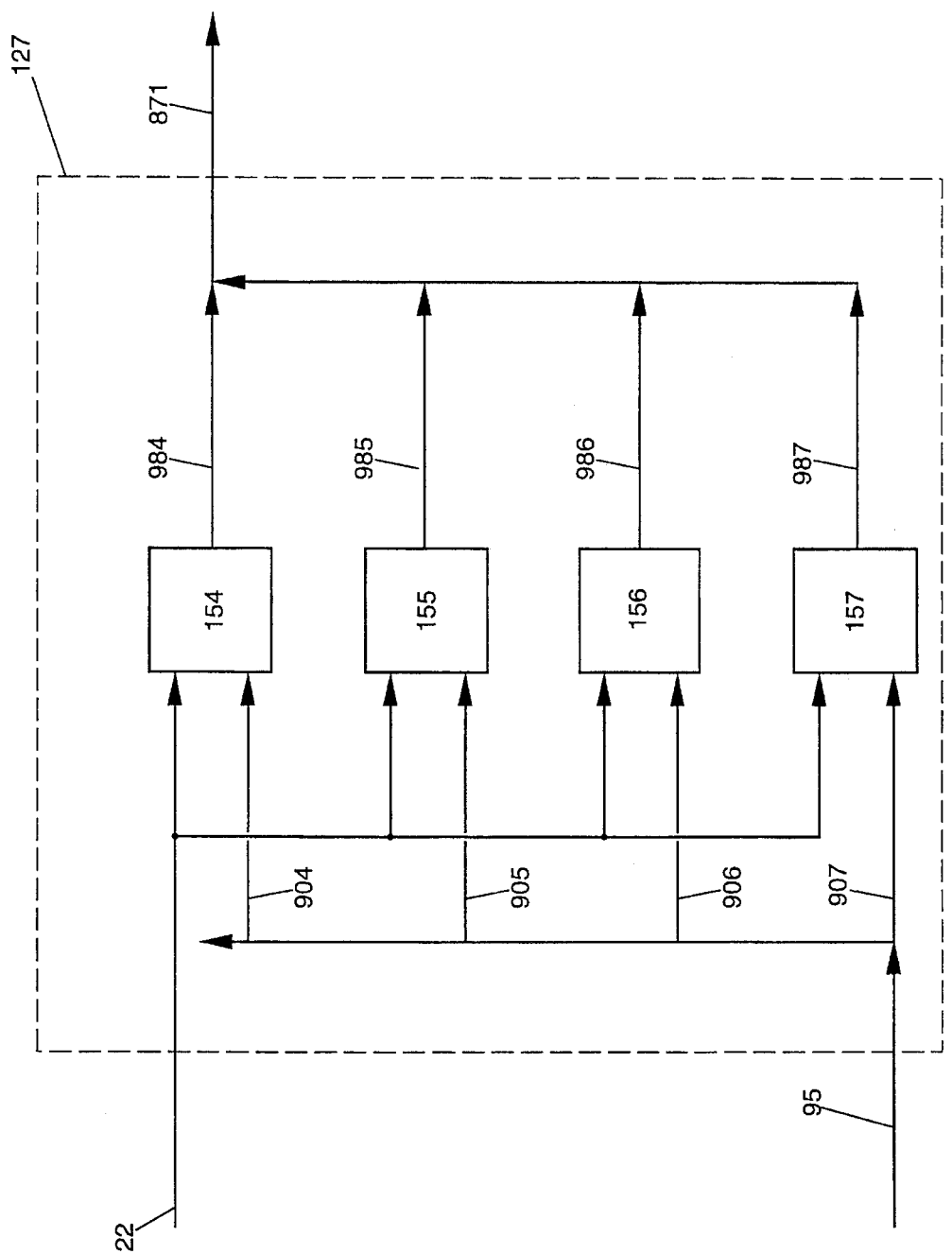

FIG. 10 shows another portion of the laser stabilization circuitry which determines data of the first characteristic signal pulse. The signal on line 22 is provided to the sample-and-hold circuits 154, 155, 156 and 157. A beat signal on line 904 (derived from the system beat 95) is provided to the sample-and-hold circuit 154. The beat signal 904 is indicative of the beginning of the first characteristic signal pulse. A beat signal on line 905 (derived from the system beat 95) is provided to the sample-and-hold circuit 155. The beat signal at line 905 indicates the end of the first quarter of the first characteristic signal pulse. A beat signal on line 906 (derived from the system beat 95) is provided to the sample-and-hold circuit 156. The beat signal at line 906 indicates the middle of the first characteristic signal pulse. A beat signal at line 907 (derived from the system beat 95) is provided to the sample-and-hold circuit 157. The beat signal 907 is indicative of the end of the third quarter of the first characteristic signal pulse.

The sample-and-hold circuit 154 samples the signal on line 22 upon receipt of the signal on line 904. The sample-and-hold circuit 155 samples the signal on line 22 upon receipt of the signal on line 905. The sample-and-hold circuit 156 samples the signal on line 22 upon receipt of the signal on line 906. The sample-and-hold circuit 157 samples the signal on line 22 upon receipt of the signal on line 907.

The output signal 984 of sample-and-hold circuit 154, the output signal 985 of sample-and-hold circuit 155, the output signal 986 of sample-and-hold circuit 156, and the output signal 987 of sample-and-hold circuit 157 are combined to form a combined output signal on line 871.

The Laser Stabilization, Part 3

Figure 11:
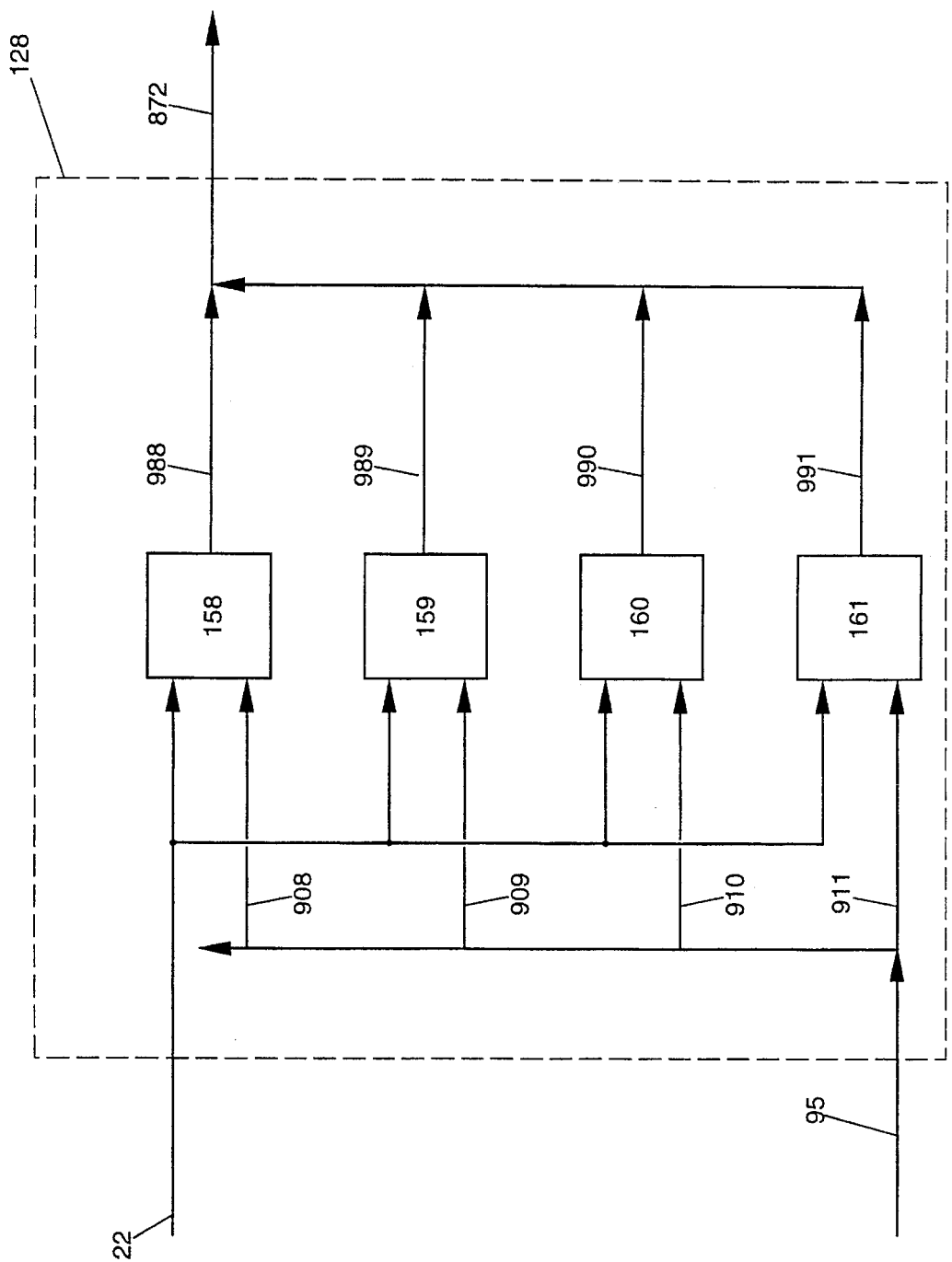

FIG. 11 shows another portion of the laser stabilization circuitry for determining data of the second characteristic signal pulse. The signal on line 22 is passed to sample-and-hold circuits 158, 159, 160 and 161. Derived from the system beat signal 95, a beat signal on line 908 is provided to the sample-and-hold circuit 158. The beat signal on line 908 indicates the beginning of the second characteristic signal pulse. Derived from the system beat signal 95, the beat signal on line 909 is provided to the sample-and-hold circuit 159. The beat signal on line 909 indicates the end of the first quarter of the second characteristic signal pulse. Derived from the system beat signal 95, a beat signal on line 910 is provided to the sample-and-hold circuit 160. The beat signal on line 910 indicates the middle of the second characteristic signal pulse. Derived from the system beat signal 95, a beat signal on line 911 is provided to the sample-and-hold circuit 161. The beat signal on line 911 indicates the end of the third quarter of the second characteristic signal pulse.

The sample-and-hold circuit 158 samples the signal on line 22 upon receipt of the signal on line 908. The sample-and-hold circuit 159 samples the signal on line 22 upon receipt of the signal on line 909. The sample-and-hold circuit 160 samples the signal on line 22 upon receipt of the signal on line 910. The sample-and-hold circuit 161 samples the signal on line 22 upon receipt of the signal on line 911.

The output signal on line 988 of sample-and-hold circuit 158, the output signal on line 989 of sample-and-hold circuit 159, the output signal on line 990 of sample-and-hold circuit 160, and the output signal on line 911 of sample-and-hold circuit 161 are combined to form a combined output signal at line 872.

Laser Stabilization, Part 4

Figure 12:
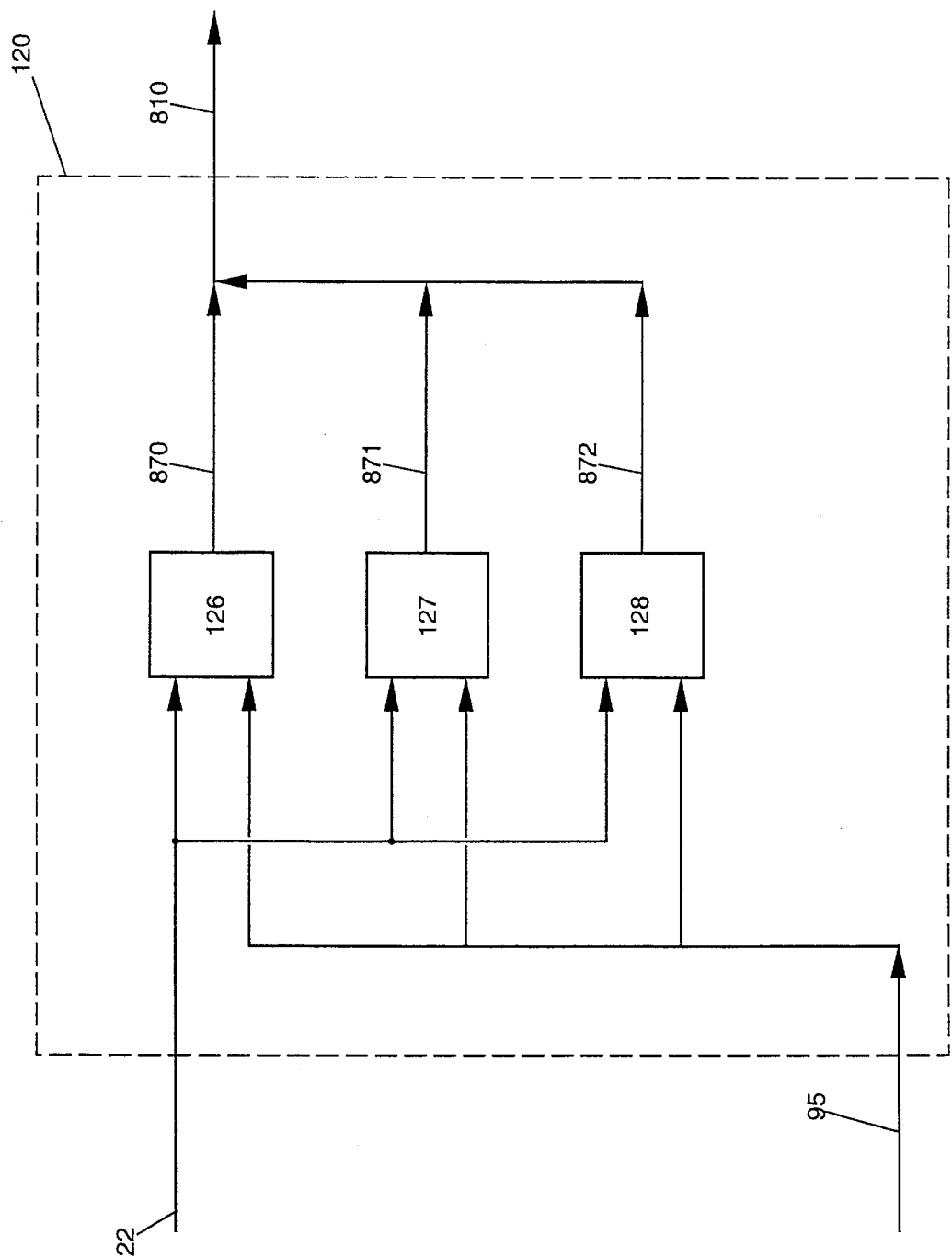

FIG. 12 shows a sample-and-hold circuit 120 for the detection of the reference signal. The signal on line 22 is provided to the sample-and-hold circuits 126, 127 and 128. The system beat signal on line 95 is provided to the sample-and-hold circuits 126, 127 and 128. The output signal at line 870 of sample-and-hold circuit 126, the output signal at line 871 of sample-and-hold circuit 127, and the output signal at line 872 of sample-and-hold circuit 128 are combined to form a combined output signal at line 810.

The sample-and-hold circuit 126 samples the signal on line 22 during the uncharacteristic signal pulse. The sample-and-hold circuit 127 samples the signal on line 22 during the first characteristic signal pulse. The sample-and-hold circuit 128 samples the signal on line 22 during the second characteristic signal pulse.

Laser Stabilization, Part 5

Figure 13:
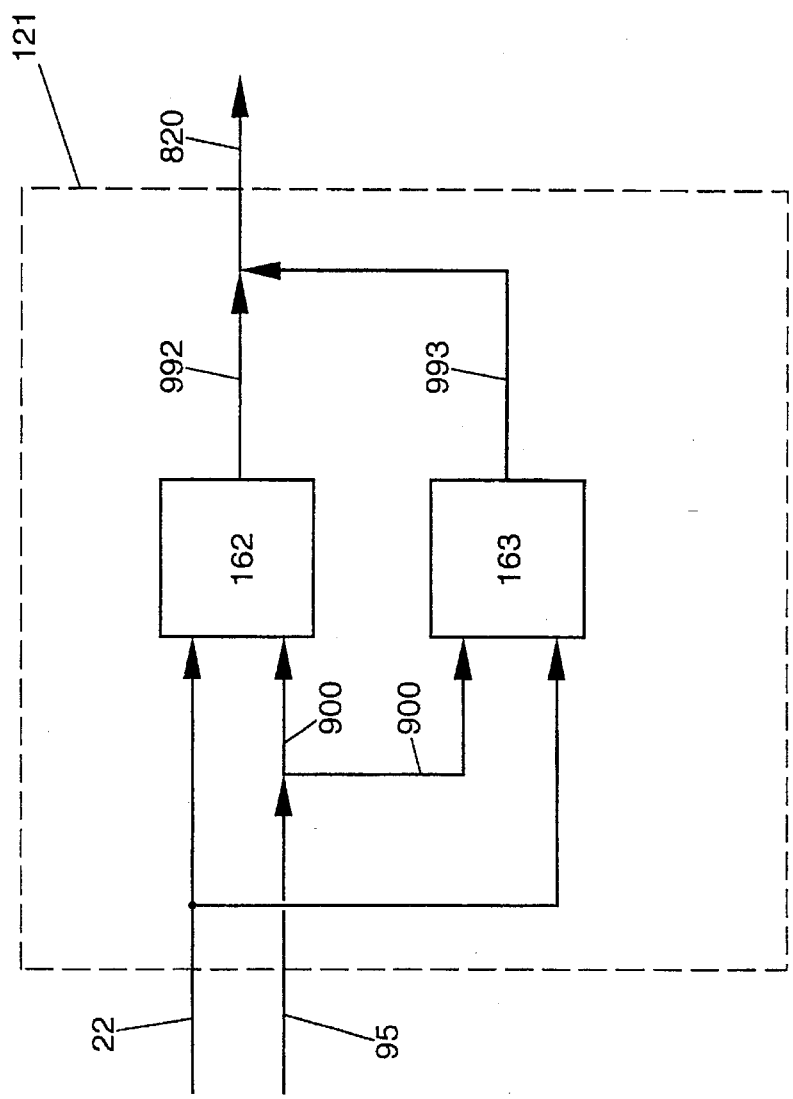

FIG. 13 shows a rectifier circuit 121 for laser stabilization (see also FIG. 4). The signal on line 22 is provided to rectifier 162 and to a peak value detector 163. A beat signal on line 900 (derived from the system beat signal 95) is provided to the rectifier 162 and the peak value detector 163. The output signal on line 992 of the rectifier 162 and the output signal on line 993 of the peak value detector are combined to form a signal on line 820.

The rectifier 162 rectifies the signal on line 22 and determines the mean value of the signal amplitude. The signal on line 900 is indicative of the signal period. The peak value detector 163 determines the peak value of the signal on line 22 within the signal period.

Laser Stabilization, Part 6

Figure 14:
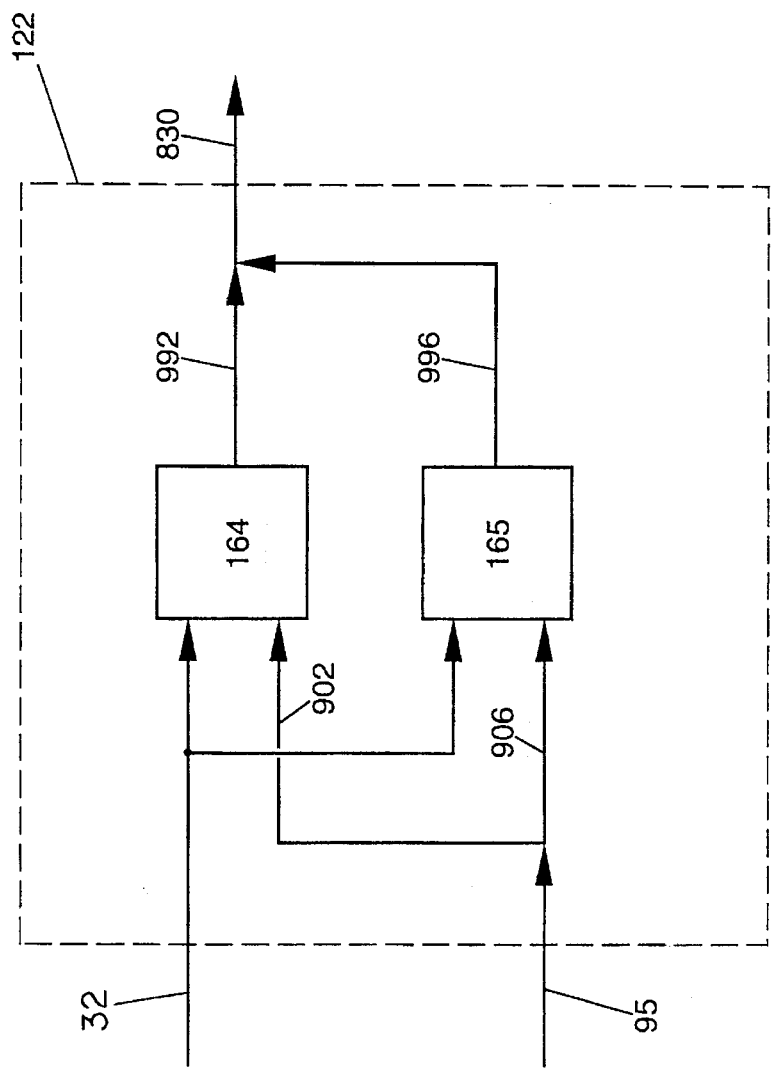

FIG. 14 shows sample-and-hold circuitry for the signal on line 32 corresponding to the calibration path 7. As shown, the signal on line 32 is provided to sample-and-hold circuits 164 and 165. Derived from the system beat signal 95, a beat signal on line 902 is provided to sample-and-hold circuit 164 and a beat signal on line 906 is provided to sample-and-hold circuit 165. The output signal on line 992 from sample-and-hold circuit 164 and the output signal on line 996 from sample-and-hold circuit 165 are combined to form a signal on line 830.

Laser Stabilization, Part 7

Figure 15:
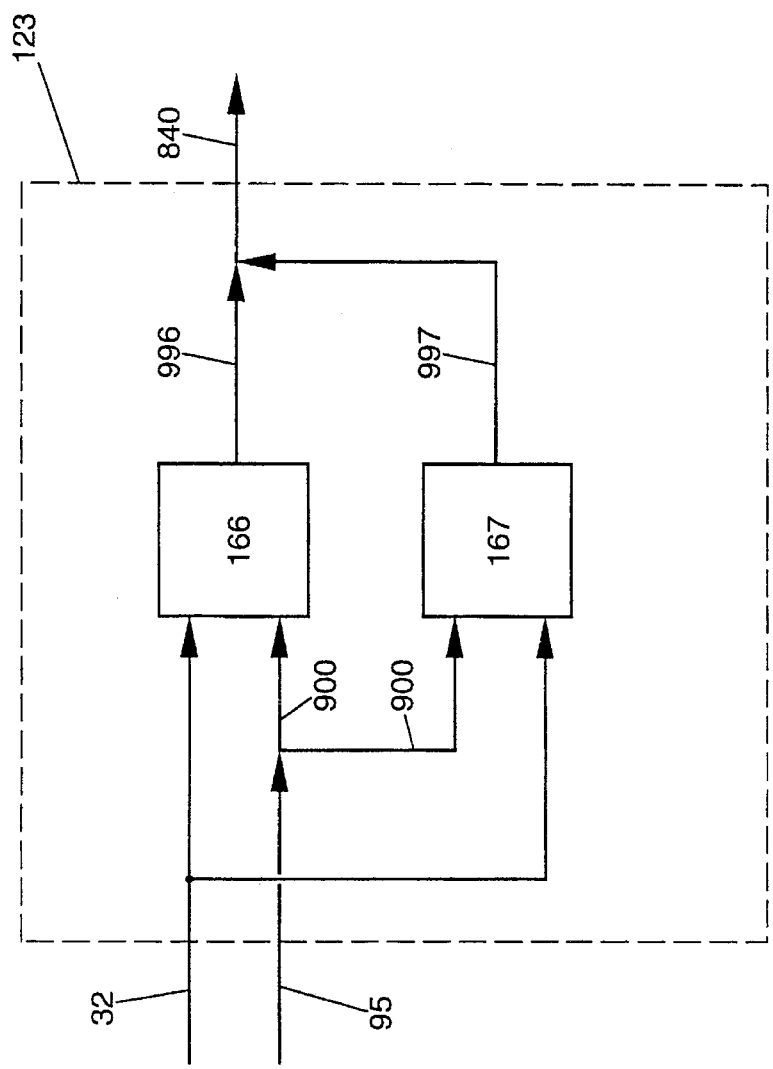

FIG. 15 shows rectifier circuit 123 of the laser stabilization section in greater detail. The signal on line 32 is provided to rectifier 166 and to peak value detector 167. Derived from the system beat signal 95, a beat signal on line 900 is provided to the rectifier 166 and to the peak value detector 167. The output signal of line 996 and the output signal on 997 are combined to form a signal on line 840.

The rectifier 166 rectifies the input signal on line 32 and determines the mean value of the signal amplitude within a signal period given by the beat signal on line 900. The peak value detector 167 determines the peak value in the signal on line 32 occurring within the signal period.

Laser Stabilization, Part 8

Figure 16:
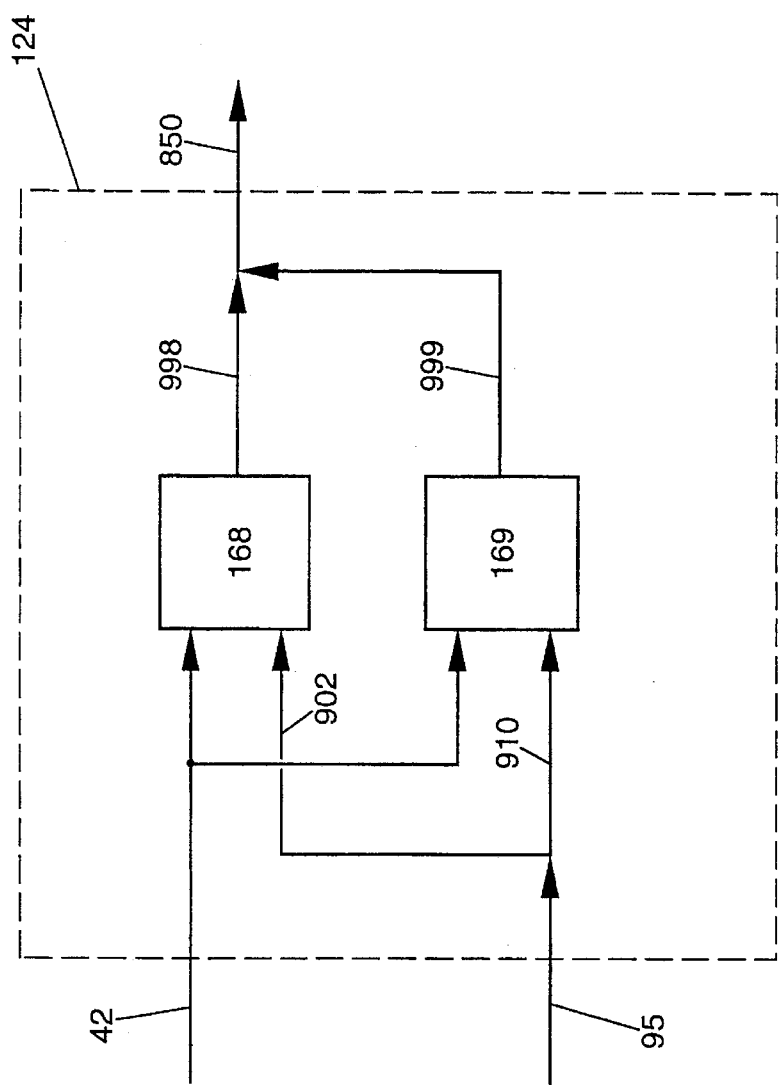

FIG. 16 shows sample-and-hold circuitry for the signal on line 42 of the calibration path 8. The signal on line 42 is provided to sample-and-hold circuits 168 and 169. Derived from the system beat signal 95, a beat signal on line 902 is supplied to sample-and-hold circuit 168 and a beat signal on line 906 is supplied to the sample-and-hold circuit 169.

The output signal 998 of sample-and-hold circuit 168 and the output signal 999 of sample-and-hold circuit 169 are combined to form a signal on line 850.

Laser Stabilization, Part 9

Figure 17:
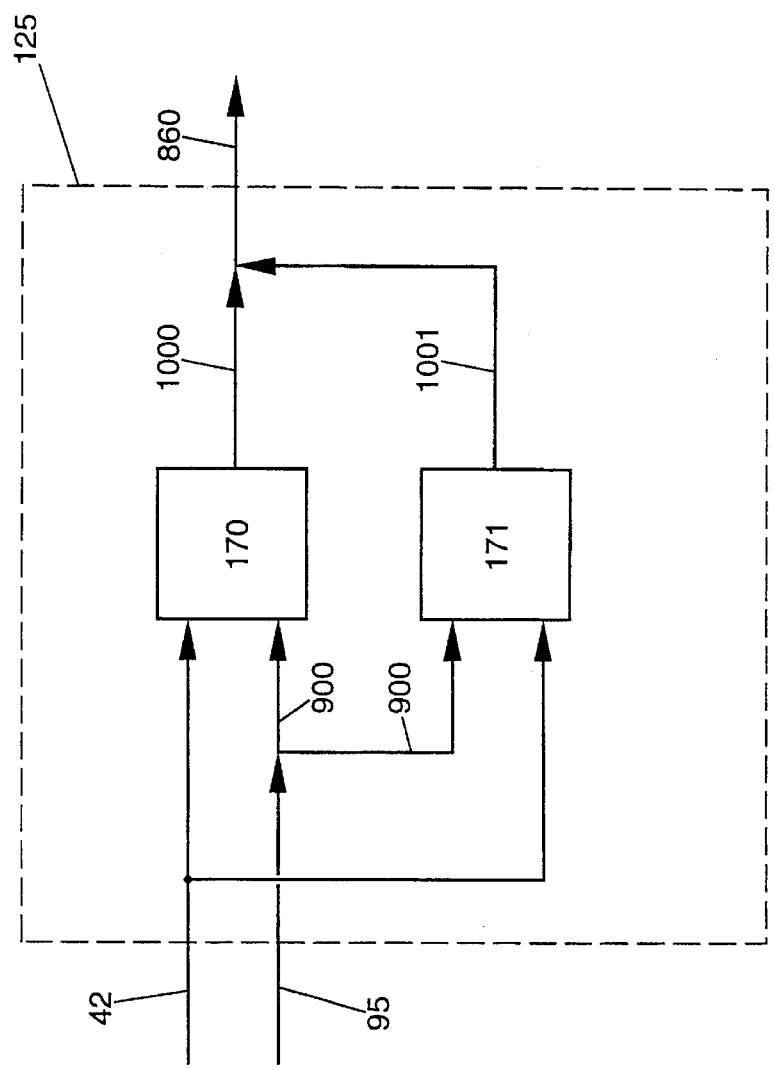

FIG. 17 shows additional rectifier circuitry 125 for laser stabilization. The signal on line 42 is passed to rectifier 170 and to peak value detector 171. Derived from the system beat signal on line 95, a beat signal 900 is supplied to rectifier 170 and to peak value detector 171. The output signal 1000 of the rectifier 170 and the output signal 1001 of the peak value detector are combined to form the signal on line 860.

The rectifier 170 rectifies the input signal on line 42 and determines the mean value of the signal amplitude within a signal period given by the bent signal on line 900. The peak value detector 171 determines the peak value of the signal 42 during the signal period.

Summary of Laser Stabilization

FIGS. 9–17 comprise the laser stabilization circuitry in the preferred embodiment. The laser used is tuned by means of a vibrating grid. The vibrating grid determines the effective resonator length of the laser and, correspondingly, the light wavelength emitted by the laser. The matter of the wavelengths on which the emission actually occurs determines the used filling of the laser. The vibrating grid can be changed once in position so that its distance from the other end of the resonance body changes and it can be set into oscillation. By the vibration of the grid the effective length of the laser and therewith its tuning is changed. While the grid is vibrating its two end positions can be adjusted. The problem of laser stabilization is the determination of these setting parameters in such manner that the laser generates exactly the desired emission.

The adjusting of the laser occurs in a process of several stages. First the three necessary laser lines are sought. Thereafter, the laser is stabilized on these lines that are found. The laser is driven with an control signal 52 from the system control 550. The beat generator is initially set to provide a default pattern The default pattern corresponds to the beat pattern to be expected, without unknown phase shift. The signals on lines 992 and 993 are then read in from the system control. The signals on lines 992 and 993 indicate with which energy the laser 1 is emitting light. Even if no laser line is tuned, these signals so indicate. The system control 550 then varies the laser drive signal until; the signals on lines 992 and 993 decrease. In other words, the system control changes the laser control until the laser emits and the emission again becomes smaller.

Now the phase position of the beat signals on lines 900, 901, 902, 903, 904, 905, 906, 907, 908, 909, 910 and 911 is changed so that the signal on line 982, the signal on line 986 and the signal on line 990 are a relative maximum, and the signal on line 980, the signal on line 984 and the signal on line 988 are a relative minimum. The signal on line 981 is approximately the same level as the signal on line 983, the signal on line 985 has approximately the same level as the signal on line 987, and the signal on line 989 has approximately the same level as the signal on line 991. When these conditions are satisfied and the beat signals on lines 900, 901, 902, 903, 904, 905, 906, 907, 908, 909, 910 and 911 have a uniform spacing of about a twelfth of the beat period, and the laser emits light on three lines.

The sample-and-hold circuits 164 and 165 simultaneously sample the signal on line 32 at the time points given by the beat signals on lines 902 and 906. The output signal on line 992 corresponds to the signal on line 32 at the maximum of the first signal pulse. The signal on line 996 corresponds to the signal level from the signal on line 32 in the maximum of the second signal pulse. As noted above, the signal on line 32 is derived from the detector 30 which is positioned proximate the calibration path 7. The signal level of the signal on line 992, therefore, will approximately correspond to the signal level of the signal on line 982 while, with correct laser tuning, the signal level of the signal on line 996 will be less than the signal level of the signal on line 986. Simultaneously, with respect to the sample-and-hold circuits 168 and 1969, the signal on line 42 is sampled at the times according to the beat signals on lines 902 and 910. The signal on line 998 corresponds consequently to the signal level of the signal on line 42 in the maximum of the first signal pulse. The signal on line 999 corresponds to the signal level of the signal on line 42 at the maximum of the third signal pulse. The signal on line 42 is derived from the detector 40 positioned proximate the calibration path 8. The signal level of the signal on line 998, therefore, will approximately correspond to the signal level of the signal on line 982, while, with correct laser tuning, the signal level of the signal on line 999 will be less than the signal level of the signal on line 990.

When all these conditions are fulfilled, the laser correctly tuned. In all other cases, the control signal on line 52 must be varied.

After the three laser lines are found, the laser is stabilized. Small variations in the signal on line 52, however, detune the laser. As soon as one of the above conditions worsens, the direction of the detuning is reversed. The laser tends to drift, therefore, about its optimal operating point, without ever abandoning it entirely. If the influence of laser detuning becomes so great that the measurement value is invalid, then a corresponding correction of the measurement value must be performed. Since the time point of the variation is known, after an adjustment has been made, the old measurement value can be utilized until the laser is again brought to its preceding setting.

Tolerance Evaluation Circuitry

Figure 18:
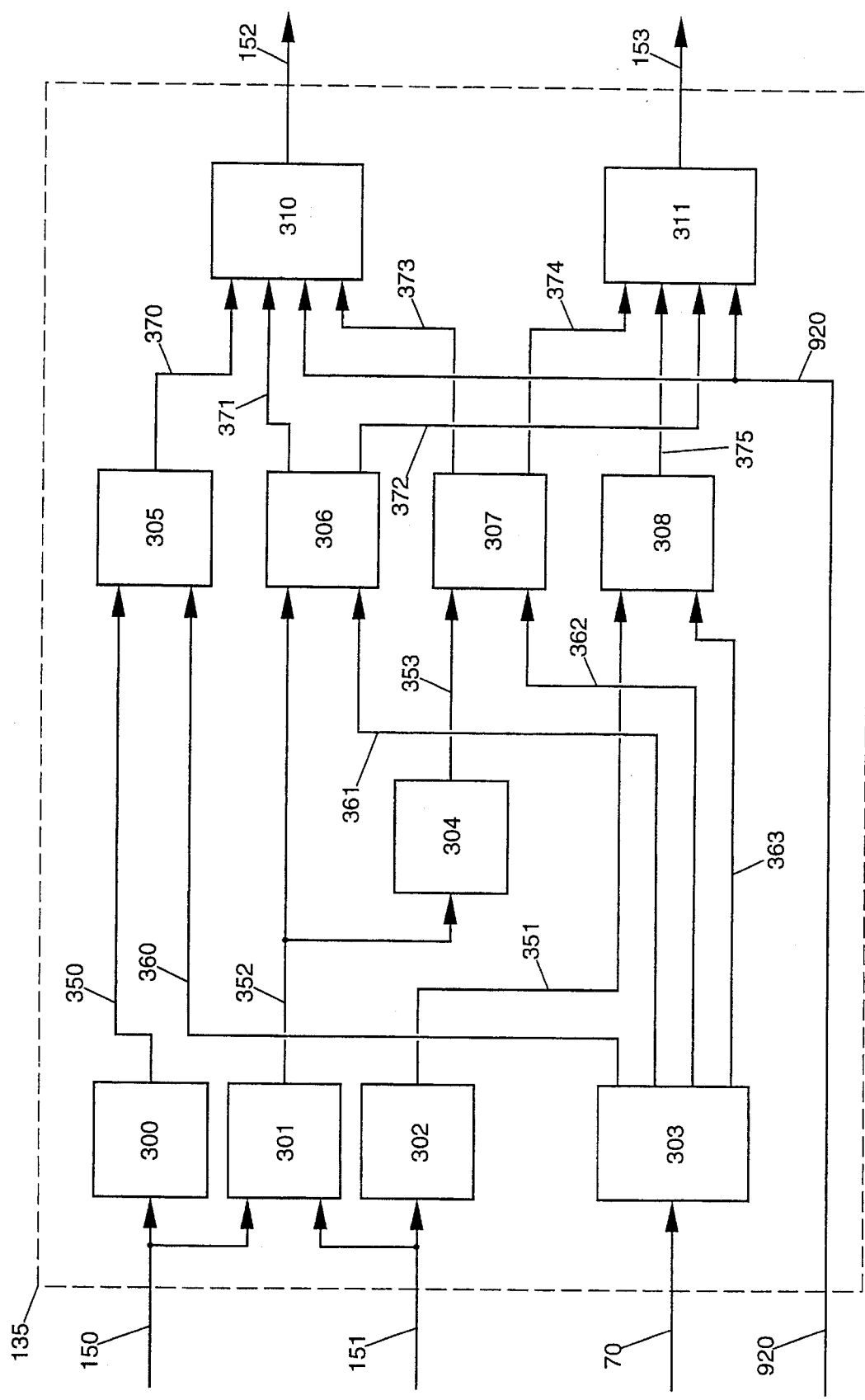
FIG. 18 is a block diagram representation of tolerance evaluation circuitry used in the circuitry of FIG. 7.

FIG. 18 shows the tolerance evaluation circuitry 135 in greater detail. The signal on line 150 is provided to a differentiating circuit 300 and to a subtracter circuit 301. The signal on line 151 is provided to a differentiator 302 and to the subtracter 301. The signal 150 is derived from the signal detector proximate the measuring path 5. The signal 151 is derived from the signal of the detector 20 proximate the reference path 6.

The differentiator 300 obtains the first derivative of the signal on line 150. The differentiator 302 likewise obtains the first derivative of the signal on line 151. The subtracter 301 provides a difference signal on line 352 from the signals 150 and 151.

The differentiator 300 provides an output signal on a line 350 to a window discriminator circuit 305. The subtractor 301 provides the output signal on line 352 to the differentiator circuit 304 and to a window discriminator circuit 306. The differentiator 302 provides an output signal on line 351 to a window discriminator circuit 308. The differentiator 304 obtains the first derivative of the difference signal on line 352. The differentiator 304 provides this output on a line 353 to window discriminator circuit 307.

The data signal on line 70 passed to a limit value storage unit 303. In this way, the system control 550 supplies data to the tolerance evaluation circuitry 135 corresponding to the current limit values of the signals on lines 350, 351, 352 and 353.

The limit value storage unit 303 provides an output data signal on a line 360 to window discriminator 305. The limit value storage unit 303 also provides an output data signal on a line 361 to the window discriminator 306. The limit value storage unit 303 also provides an output data signal on a line 362 to the window discriminator 307. The limit value storage unit 303 provides a further output data signal on a line 363 to window discriminator 308.

The signal on line 360 represents the signal range within which the signal on line 350 is evaluated as valid. The signal on line 361 represents the signal range within which the signal on line 352 is evaluated as valid. The signal on line 362 represents the signal range within which the signal on line 353 is evaluated as valid. The signal on line 363 represents the signal range within which the signal on line 351 is evaluated as valid.

The window discriminator 305 provides an output signal on a line 370 to a gating circuit 310. The window discriminator 306 also provides an output signal on a line 371 to the circuit 310. The window discriminator 306 also provides an output signal on line 372 to the circuit 310. The window discriminator 307 provides an output signal on a line 373 to the circuit 310. The window discriminator 307 supplies an output signal on a line 374 to a gating circuit 311. The window discriminator 308 also provides an output signal on a line 375 to the circuit 311.

The beat signal on line 920 is supplied to the circuits 310 and 311. This signal is indicative of the end of an evaluation signal period. If the current signal level of the signal(s) 150 and 151 determined to be valid, then at the end of the evaluation signal period the beat signal 920 is passed as the signals on lines 152 and 153. In other words, the circuit 310 passes the beat signal received on line received on line 920 as the output signal on line 152 when the discriminator output signals 370, 371 and 373 evaluate the input signals 150 and 151 as valid. The circuit 311 passes the beat signal received on line 920 as the output signal on line 153 when the discriminator output signals 374, 375 and 372 evaluate the input signals on lines 150 and 151 as valid. If one of the window discriminators 305, 306, 307 and 308 does not evaluate a parameter of the input signals 150 and 151 as valid, the beat signal on line 920 is inhibited.

Figure 19:
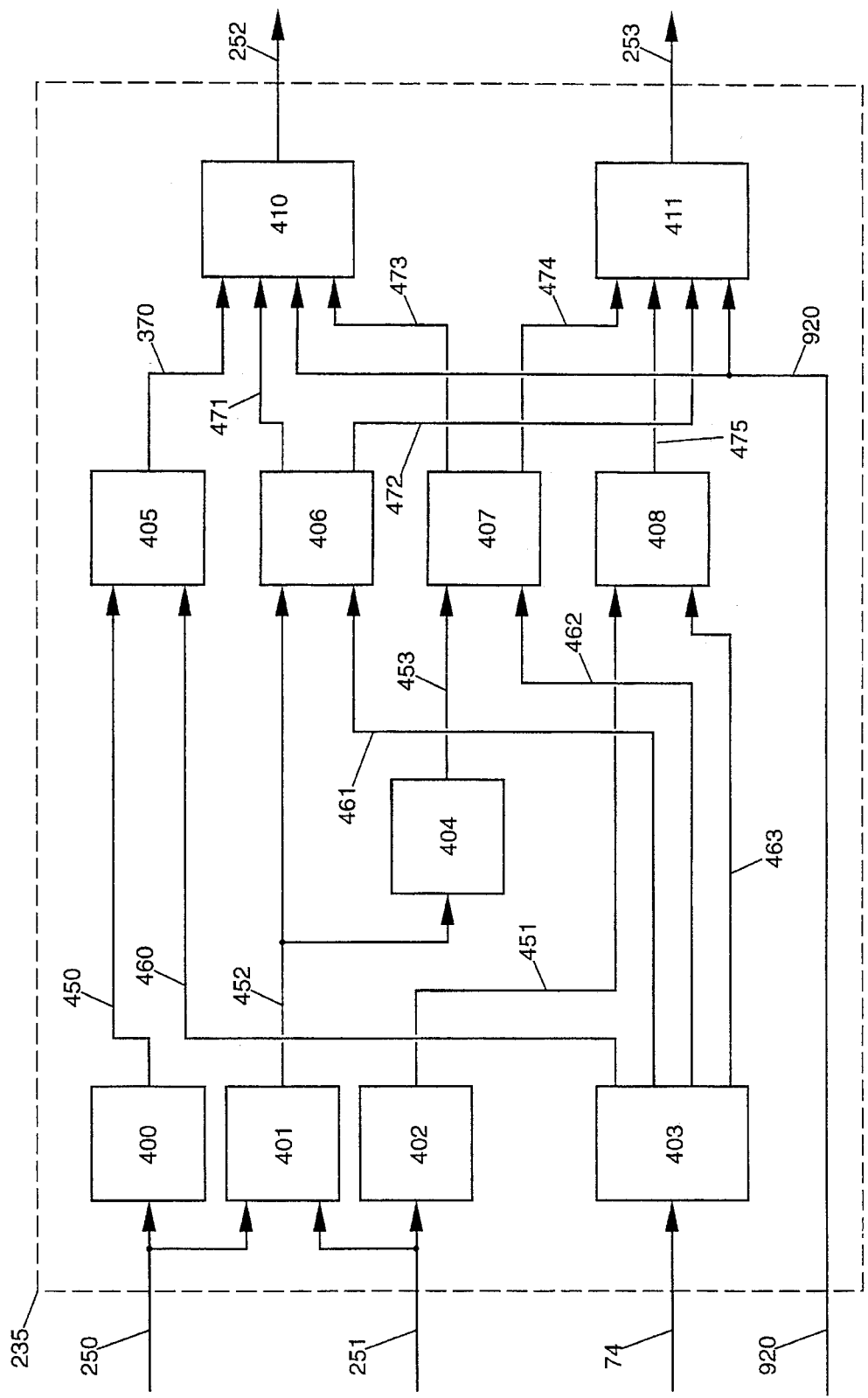
FIG. 19 is a block diagram representation of tolerance evaluation circuitry used in the circuitry of FIG. 8.

FIG. 19 describes the tolerance evaluation circuitry 235. The signal on line 250 is supplied to differentiating circuit 400 and to subtracter 401. The signal on line 251 is supplied to differentiator 402 and to subtracter 401. The signal on line 250 is derived from the signal of the detector 10 proximate the measuring path 5. The signal on line 251 is derived from the signal of the detector 20 proximate the reference path 6.

The differentiator 400 obtains the first derivative of the signal on line 250. The differentiator 402 obtains the first derivative of the signal on line 251. The subtracter 401 provides a difference signal from the signals 250 and 251.

The differentiator 400 provides an output signal on line 450 to the window discriminator 405. The subtracter 401 provides the difference signal at line 453 to differentiator 404 and to window discriminator 406. The differentiator 402 provides an output signal to window discriminator 408. The differentiator 404 obtains the first derivative of the signal on line 452. The differentiator 404 provides an output on line 453 to window discriminator 407.

The data signal on line 70 is supplied to limit value storage unit 403. In this way, the system control 550 provides data to the tolerance evaluation circuitry 235 concerning the current limit values of the signals on lines 450, 451, 452 and 453. The limit value storage unit 403 provides a data signal on line 460 to window discriminator 405. The limit value storage unit 403 provides a data signal on line 461 to window discriminator 406. The limit value storage unit 403 also provides data signals on lines 462 and 463 to window discriminator 407 and window discriminator 408, respectively.

The signal on line 460 represents the signal range within which the signal on line 450 is evaluated as valid. The signal on line 461 represents the signal range within which the signal on line 452 is evaluated as valid. The signal on line 462 represents the signal range within which the signal on line 453 is evaluated as valid. The signal on line 463 represents the signal range within which the signal on line 451 is evaluated as valid.

The window discriminator circuits 405, 406, 407 provide output signals on lines 470, 471, 473 to gating circuit 410. The window discriminators 406, 407 and 408 provide output signals On lines 472, 473, 475 to gating circuit 411. The beat signal on line 920 is also supplied to the gating circuits 410 and 411. The beat signal on line 920 is indicative of the end of an evaluating signal period. If the current signal level of the signal(s) 250 and 251 are valid, the beat signal on line 920 is passed as signals 252 and 253.

The gating circuit passes the beat signal at line 920 if the signals at lines 470, 471 and 473 evaluate the input signals 250 and 251 as valid. The gating circuit 411 likewise passes the beat signal at line 920 if the signal at lines 474, 475 and 472 evaluate the input signals 250 and 251 as valid. If one of the window discriminators 405, 406, 407 and 408 evaluates only one parameter of the input signals 250 and 251 as invalid, the beat signal 920 is inhibited.

Alternative Measurement Value Processing

Figure 20:
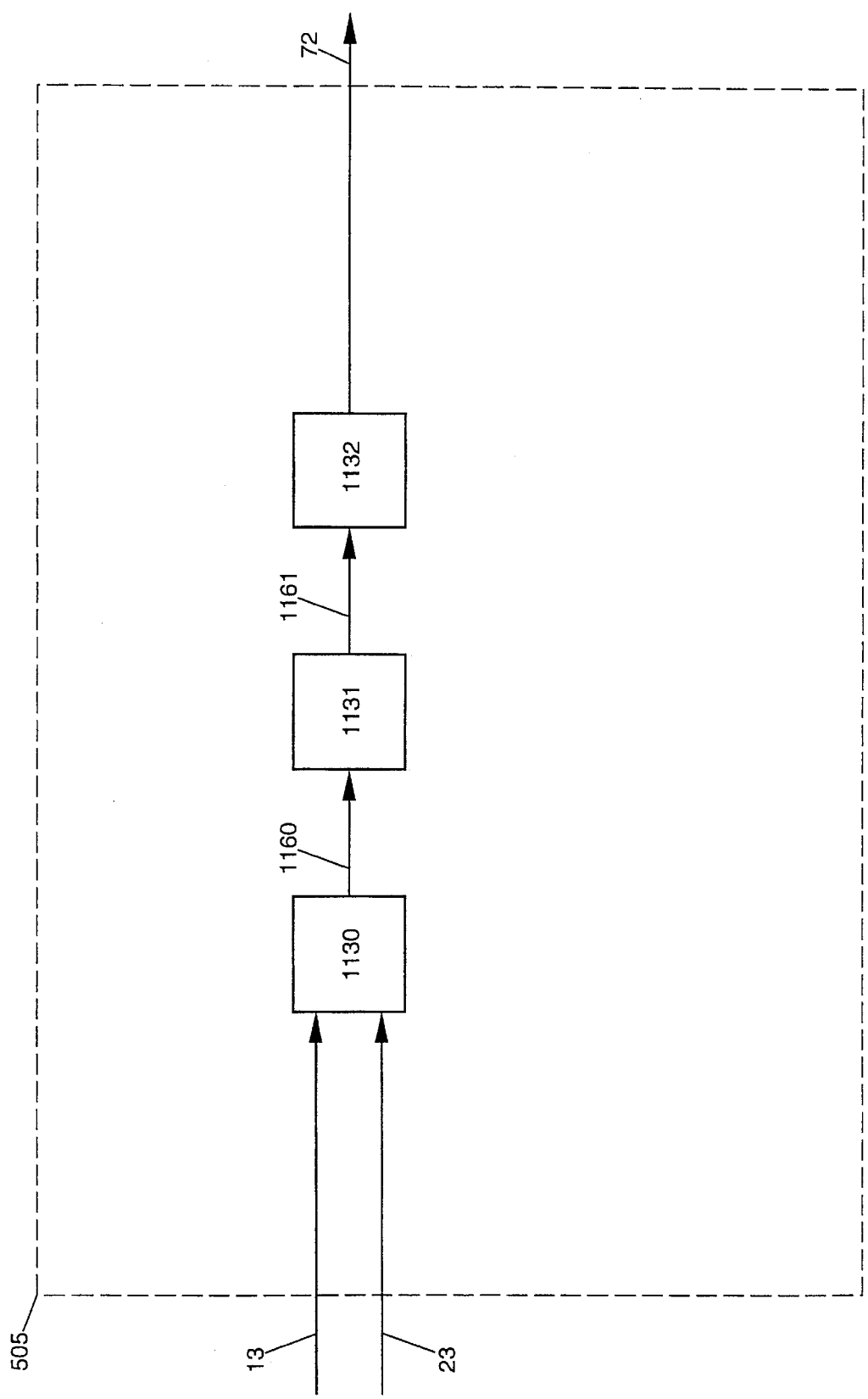
FIG. 20 is a block diagram representation of alternative measurement-value preparation circuitry.

FIG. 20 shows one preferred alternative to the measurement value processing shown in FIGS. 7 or 8. A subtracter 1130 receives the signals on lines 13 and 23. The subtracter 1130 provides a difference signal output on line 1160 to a Fast Fourier Transform (FFT) analyzer 1131. The FFT analyzer 1131 provides an output signal on a line 1161 to amplifier 1132.

The FFT analyzer 1130 is arranged in such a way that its output appears as a signal with half the pulse repetition occurring in the two input signals 13 and 23. The amplitude of this signal is proportional to the concentration of the selected gas on the measuring path 5.

Alternative Laser Stabilization

According to the state of technology, as known from EP 89 906 096.0, the electrical signal of a detector may also be dissected into its Fourier components. If the laser in particular is correctly adjusted to the two selected wavelengths, the light emitted in the reference path, on which the gas whose concentration has to be determined in the measuring path is not present, is not damped. The light ray in the calibration path, in which there is a vessel filled with the selected gas, will be damped with one light pulse and will not be damped with the other.

Thus, the Fourier spectrum of the electric signal from the detector of the reference path primarily contains only portions at that frequency which is derived from the pulse beat frequency. The other spectral portions result primarily from the differing emissions of the laser in the two wavelengths used.

The Fourier spectrum of the electric signal from the detector of the calibration path will therefore contain signal portions which are derived from the pulse beat frequency and half of the pulse beat frequency.

According to the invention the laser is correctly adjusted when in the spectrum those portions from the signal of the reference path have a maximum which have been derived from the pulse beat frequency, and those portions have a minimum which have been derived from half of the pulse beat frequency. In other words, the odd numbered spectral portions have a minimum, while the even numbered portions have a maximum. Simultaneously, all even and odd numbered portions must have a relative maximum in the spectrum from the signal of the calibration path. If there is such a high concentration of the selected gas or calibration substance, in the calibration path, the characteristic radiation pulse is absorbed completely. Then, no more even numbered portions will appear in the spectrum of the calibration path signal, even when the laser is adjusted correctly.

Figure 21:
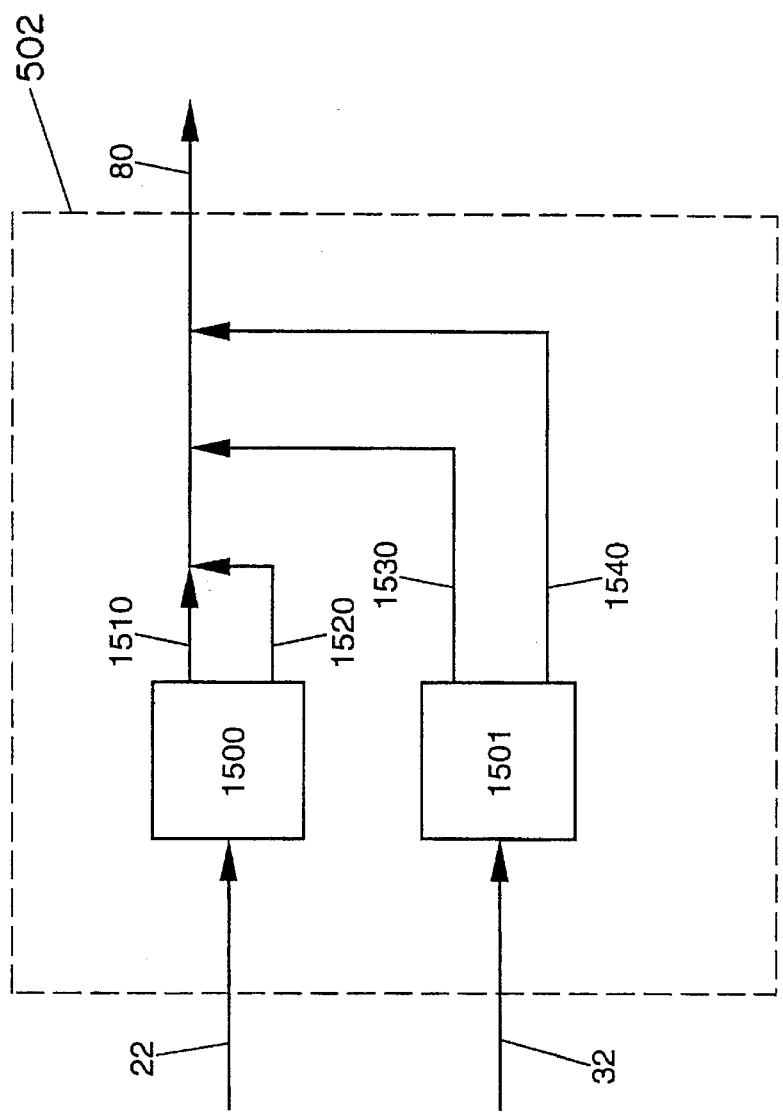
FIG. 21 is a block diagram representation of alternative laser stabilization circuitry.

FIG. 21 shows a preferred alternative form of laser stabilization. The signal on line 22 is supplied to an FFT analyzer 1500. The signal on line 32 supplied to a second FFT analyzer 1501. The output signals 1510 and 1520 of the FFT analyzer 1500 as well as the output signals 1530 and 1540 of the FFT analyzer 1501 are combined to form an output signal on line 80.

The FFT analyzer 1500 conducts a Fourier analysis of the signal on line 22 as will be understood by those skilled in the art. As a result of the Fourier analysis, the signal on line 1510 has a frequency corresponding to half the pulse repetition frequency. The signal at line 1520 has a frequency corresponding to the pulse repetition frequency.

The FFT analyzer 1501 carries out a Fourier analysis of the signal on line 32. As a result, the signal at line 1530 has a frequency corresponding to half the pulse repetition frequency. The signal at line 1540 has a frequency corresponding to the pulse repetition frequency.

In this embodiment, the laser emits energy of two light wavelengths. Alternatively, prior to laser tuning, the signals on lines 22, 32 and 42 may be subdivided into signal pairs according the same methodology employed by circuit 504, in order to obtain the signals on lines 13 and 23 and 14 and 24 from the signals on lines 12 and 22, respectively. Processing of the signal on line 42 is simplified when two signal pulses are utilized.

The signal on line 22 is derived from the light beam that radiates through the reference path 6. The signal on line 32 is derived from the light beam that radiates through the calibration path 7. The signal on line 22, consequently, is a direct image of the laser emission. The signal on line 32, during the emission of the uncharacteristic light beam, is likewise an image of the laser emission. During the emission of the characteristic light beam, this signal is strongly damped in the calibration path. The characteristic light pulse is consequently reduced in the signal on line 32.

If the signal on line 22 of the correctly balanced laser is resolved into its spectral components, then it demonstrates that substantially only constituents are present at the same frequency which corresponds to the pulse repetition frequency of the signal on line 22. All other constituents are present only in dependence on the pulse waveform. If the signal on line 32 of the correctly balanced laser is resolved into its spectral components, then it demonstrates the presence of substantially only constituents at the half frequency and at the whole frequency (corresponding to the pulse repetition frequency of the signal on line 32). If the laser is imbalanced, the spectral composition of the signals on lines 22 and 32 also changes.

For a set-up operation, the laser 1 is driven with a control signal on line 52, which is varied until the signal on line 1520 reaches a maximum and the signal on line 1510 a minimum, while the signal on line 1530 reaches a maximum and the signal on line 1540 maximum. This is always the case when the signal pulses of the signal on line 32 appear at maximal amplitude; a signal pulse on line 32 appears with maximal amplitude during the second signal pulse of the signal on line 32.

This is the case when the laser emits once with the characteristic light wavelength and once in the uncharacteristic light wavelength. The characteristic light pulse is then damped on the calibration path, while the other light pulses pass undamped to the detectors 20 and 30.

For the long-time stabilization, here, too, the laser is slightly detuned continuously in operation. The detuning direction is always reversed when the signals on lines 1510, 1520, 1530 and 1540 deviate in correspondence to the above condition.

Detector Signals And Timing

Figure 22:
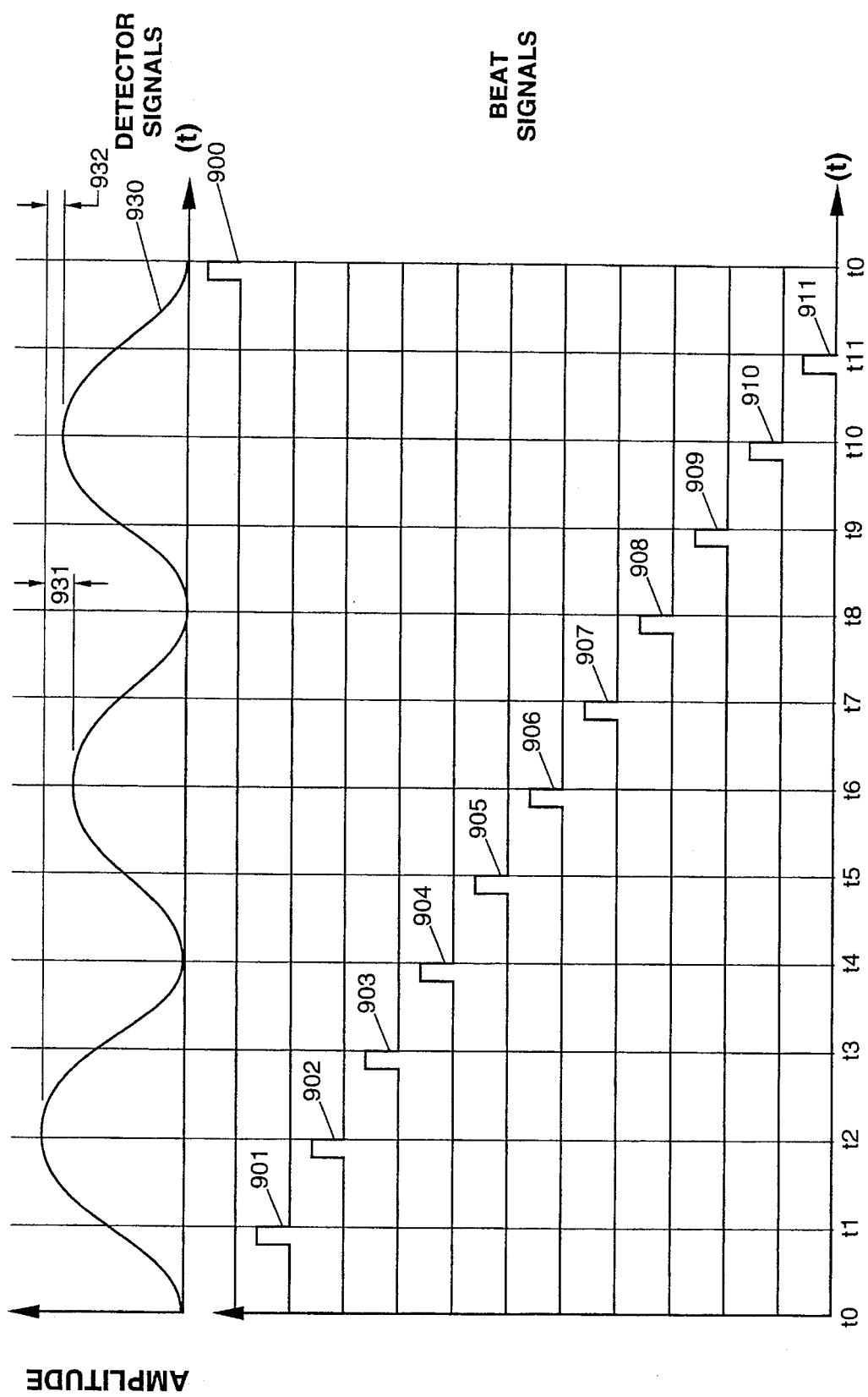
FIG. 22 is a timing diagram illustrating the interrelationship of pulse and detector signals.

FIG. 22 shows the ideal relationship of the system pulse or beat signals 900, 901, 902, 903, 904, 905, 906, 907, 908, 909, 910 and 911 to the detector signals 11, 21, 31 and 42, as well as to signals 32, 22, 32 and 42 derived from the detector signals. The signal 930 corresponds to the waveform to be expected of the signals 11, 21, 31, 41, 12, 22, 32 and 42.

The signal 930 represents three pulse trains. The first pulse is represented as an uncharacteristic pulse for simplification. The uncharacteristic pulse is generated by the light pulse wavelength that is uncharacteristic for all the substances on the measuring path 5. The second pulse is the first characteristic pulse. The first characteristic pulse is generated by the light pulse having a wavelength characteristic for the gas which is present in the vessel on the calibration path 7. The third pulse is represented as the second characteristic pulse. The second characteristic pulse is generated by the light pulse having a wavelength characteristic of the gas which is present in the vessel on the calibration path 8.

The first pulse is directly proportional to the emission of the laser emitting light of the uncharacteristic light wavelength. During the passage of the light beam of uncharacteristic light wavelength through the measuring path, the beam is weakened—if at all—only by a constant factor. The second pulse is proportional to the laser emission of the first characteristic light wavelength, weakened by the absorption of the light beam impinging on the measuring path 5. The absorption is dependent on the concentration of the selected gas which is present in the vessel on the calibration path, on the measuring path 5 and, if a cross-sensitivity is present, on the concentration of the selected gas present in the vessel of the calibration path 8. The third pulse is emitted proportionally to laser emission of the second characteristic wavelength, weakened by the absorption of the light beam on the measurement path 5. The absorption is dependent on the concentration of the selected gas which is present in the vessel on the calibration path 8.

The difference in amplitude between the first and the second pulses denoted by signal 931, consequently, is a measure of the concentration of the two gases on the measuring path 5. The difference in amplitude between the first and the third pulses denoted by arrows 932, consequently, is a measure for the concentration of the second gas on the measuring path 5.

The beat signals represented in the lower half of FIG. 22 provide synchronization of the evaluating electronic unit with the detector signals. The falling edge of beat signal 900 indicates the beginning of a new signal period and the end of the last signal period. The falling edge of beat signal 901 indicates the end of the first quarter of the uncharacteristic signal pulse. The beat signal 902 corresponds to the middle of the uncharacteristic signal pulse. The beat signal 903 corresponds to the end of the third quarter of the uncharacteristic signal pulse. The beat signal 904 corresponds to the end of the uncharacteristic pulse and the beginning of the characteristic signal pulse. The falling edge of beat signal 905 corresponds to the end of the first quarter of the first characteristic signal pulse. The falling edge of beat signal 906 corresponds to the middle of the characteristic signal pulse. The falling edge of beat signal 907 corresponds to the end of the third quarter of the first characteristic signal pulse. The falling edge of beat signal 908 corresponds to the end of the first characteristic signal pulse and the beginning of the second characteristic signal pulse. The falling edge of beat signal 909 corresponds to the end of the first quarter of the second characteristic signal pulse. The falling edge of beat signal 910 corresponds to the middle of the second characteristic signal pulse. The falling edge of beat signal 911 corresponds to the end of the third quarter of the second characteristic signal pulse. The beat signals 900, 901, 902, 903, 904, 905, 906, 907, 908, 909, 910 and 911 are adjusted by the system control so that the above phase relationship is maintained.

Signal Subdivision

Figure 23:
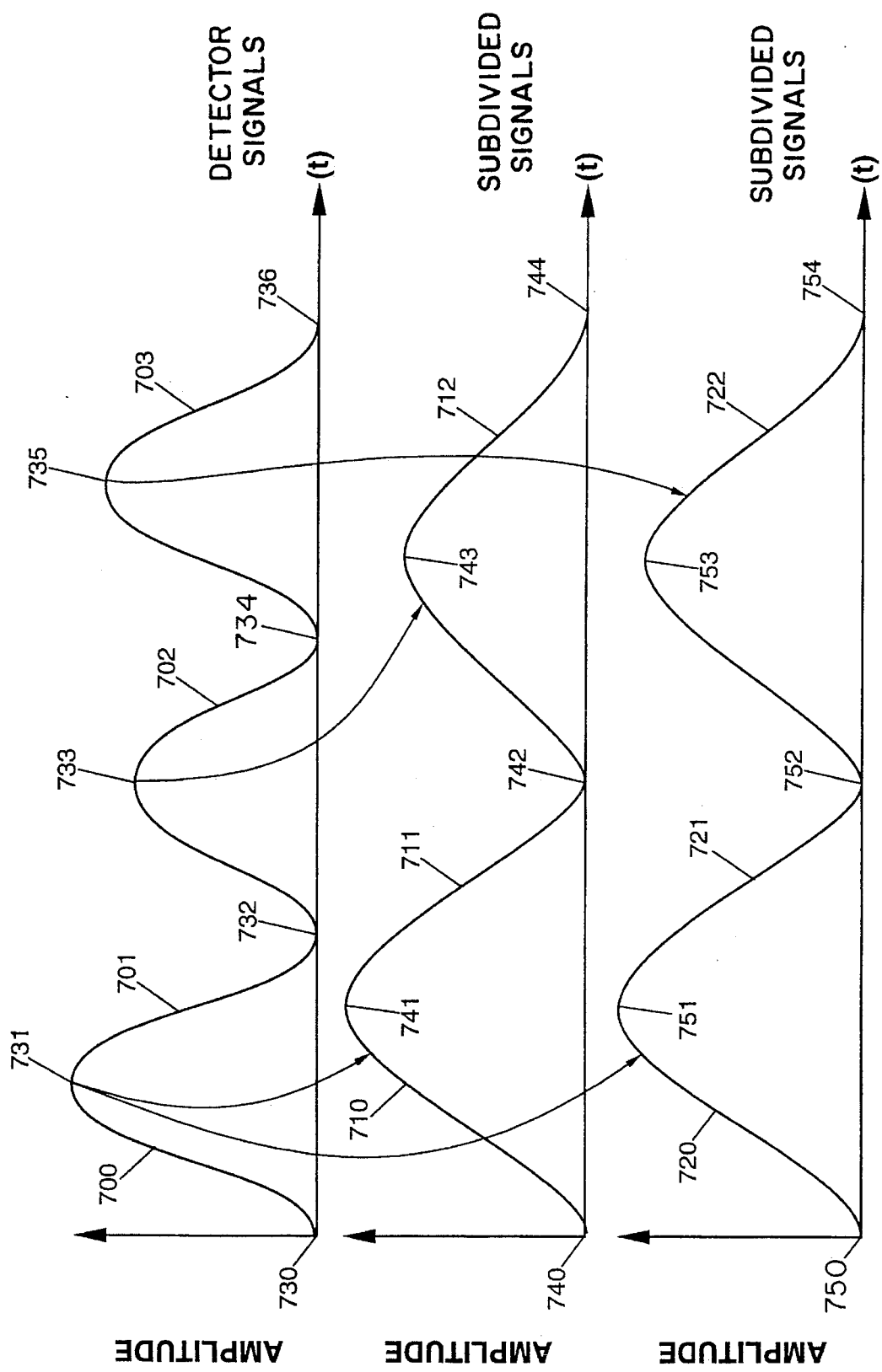
FIG. 23 is a timing diagram illustrating an idealized detector signal and its subdivision into two signals according to the invention.

FIG. 23 shows an idealized detector signal and its subdivision into two signals. The curve denoted by a line 700 corresponds to the waveform of the signals on lines 11, 21, 31, 41, 12, 22, 32 and 42. The curve denoted by a line 710 corresponds to the waveform of the signals on lines 13 and 23. The curve 720 corresponds to the curve of the signals 14 and 24.

The upper curve 700 represents a period of the idealized detector signal. The curve 700 begins, at the time denoted by a point 730, at a relative minimum. Until the time point 731, the signal level increases to a relative maximum. In the interval between the time point 731 and the time point 732, the signal level diminishes to a relative minimum. The signal pulse 701 is applied in the interval between the time points 730 and 732. In the interval between the time point 732 and the time point 733 the signal level again increases to a relative maximum. In the interval between the time point 733 and the time point 734, the signal level diminishes to a relative minimum. The signal pulse 702 is applied in the interval between the time points 732 and 734. In the interval between the time points 734 and 735, the signal level increases to a relative maximum. In the interval between the time points 735 and 736, the signal level diminishes to a relative minimum. The signal pulse 703 is applied in the interval between the time points 734 and 736. The signal period of the signal 700 has a duration beginning at the time point 730 and ending at the time point 736.

The signal levels at the time points 730, 732, 734 and 736 are not necessarily equal. Likewise, the signal levels at the time points 731, 733 and 735 are necessarily equal.

The first signal pulse 701 is generated from the emission of light by the laser 1 with the uncharacteristic light wavelength. The second signal pulse 703 is generated from the emission of light by the laser 1 with the first characteristic light wavelength. The third signal pulse is generated from the emission of light by the laser 1 with the second characteristic light wavelength. The amplitude of the signal pulse 701, in the case of all four signals 11, 21, 31 and 41 shown, corresponds to the laser emission. The amplitude of the signal pulse 702 corresponds, in the case of signal 21, to the laser emission. The amplitude of the signal pulse 702 corresponds, in the case of signal 21, to the laser emission. The amplitude of the signal pulse 702 corresponds, in the case of the signal 31, to the laser emission weakened by the absorption of the light beam on the calibration path 7, in which there is present a vessel containing a gas for which the light wavelength of the allocated light pulse is characteristic. The amplitude of the signal pulse 702, corresponds in the case of the signal 31, to the laser emission weakened by the absorption of the light beam on the calibration path 8, in which there is present a vessel with a gas for which the light wavelength of the allocated light pulse is likewise characteristic. The amplitude of the signal pulse 702 corresponds, in the case of the signal 41 to the laser emission. The amplitude of the signal pulse 703 corresponds, in the case of the signal 21, to the laser emission. The amplitude of the signal pulse 703 corresponds, in the case of the signal 31, to the laser emission. The amplitude of the signal pulse 703 corresponds, in the case of the signal 41, to the laser emission weakened by the absorption of the light beam on the calibration path 8 in which there is present a vessel containing a gas for which the light wavelength of the allocated light pulse is characteristic.

The amplitude of the signal pulse 701, in the case of signal 11, corresponds to the laser emission, possibly weakened by the constant absorption of the light beam 203 on the measuring path 5. The amplitude of the light pulse 702, in the case of signal 1, corresponds to the laser emission possibly weakened by the constant absorption of the light beam 203 on the measuring path 5 and weakened by the absorption of the gas present in the calibration path 7 and the absorption of the gas present in the calibration path 8. The absorption of the light beam 203 on the measuring path 5, by gas that is also contained in the calibration path 7, is proportional to the concentration of this gas on the measuring path 5, and proportional to the concentration of the gas which is contained in the calibration path 8. The amplitude of the signal pulse 703, in relation to signal 11, corresponds to the laser emission possibly weakened by the constant absorption of the light beam 23 on the measuring path 5 and weakened by the absorption of the light beam 203 on the measuring path 5 by the gas which is also contained in the calibration path 8. The absorption of the light beam 203 on the measuring path 5 by the gas which is also present on the calibration path 8, is proportional to the concentration of this gas on the measuring path.

The light wavelength of the light pulse allocated to the signal pulse 702 is characteristic for both the gases that are present in the vessels of the two calibration paths 7 and 8. Since, with respect to the measuring path 5, it is not possible to distinguish whether absorption occurs due to the substance that is present on the calibration path 7 or whether it is by reason of the absorption by the substance that is present on the calibration interval 8 by the light beam 203 being absorbed at the first characteristic light wavelength, one speaks generally of a "cross-sensitivity".

The middle curve 710 corresponds to the idealized waveform of the subdivided signals 13 and 23. The curve 710 begins at the time point 740 at a relative minimum. During the interval between the time points 740 and 741, the signal level increases to a relative maximum. During the interval between time points 741 and 742, the signal level diminishes to a relative minimum. The signal pulse 711 is applied in the interval between time points 740 and 742. During the interval between the time points 742 and 743 the signal level increases to a relative maximum. During the interval between the time points 743 and 744, the signal level diminishes to a relative minimum. The signal pulse 712 is applied between the time points 742 and 744.

The lower curve 720 corresponds to the idealized waveform of the subdivided signals 14 and 24. The curve 720 begins at the time point 750 at a relative minimum. During the interval between the time points 750 and 751, the signal level increases to a relative maximum. During the interval, between the time points 751 and 752, the signal level diminishes to a relative minimum. The signal pulse 721 is applied during the interval between the time points 750 and 752. Between the time points 752 and 753, the signal level increases to a relative maximum. Between the time points 753 and 754, the signal level diminishes to a relative minimum. The signal pulse 722 is applied between the time points 752 and 754.

The curves 710 and 720 are derived from the curve 700. The signal pulses 711 and 721 are derived from the signal pulse 701. The signal pulse 712 is derived from the signal pulse 702. The signal pulse 722 is derived from the signal pulse 703.

The signal period of the curves 700, 710 and 720 is equal. The amplitude of the signal pulse 711 at the time point 741 and the amplitude of the signal pulse 721 at the time points 751 correspond to the amplitude of the signal pulse 701 at the time point 731. The amplitude of the signal pulse 712 corresponds to the amplitude of the signal pulse 702 at the time point 733. The amplitude of the signal pulse 722 corresponds to the amplitude of the signal pulse 703 at the time point 735. The amplitude of the signal pulse 711 at the time point 740 and the amplitude of the signal pulse 721 at the time point 750 correspond to the amplitude of the signal pulse 701 at the time point 730. The amplitude of the signal pulse 711 at the time point 742 and the amplitude of the signal pulse 721 at the time point 752 correspond to the amplitude of the signal pulse at the time point 732. The amplitude of the signal pulse 721 at the time point 742 corresponds to the amplitude of the signal pulse 733 at the time point 732. The amplitude of the signal pulse 712 at the time point 744 corresponds to the amplitude of the signal pulse 702 at the time point 734. The amplitude of the signal pulse 722 at the time point 752 corresponds to the amplitude of the signal pulse 703 at the time point 734. The amplitude of the signal pulse 722 at the time point 754 corresponds to the amplitude of the signal pulse 735 at the time point 736.

The period of the signal pulse 701 is extended for the transformation into the signal pulses 711 and 721 in such manner that the time point 740 and the time point 750, like the time point 730, lie at the beginning of the signal period and the time point 732 is shifted such that, as is the case with time points 742 and 752, respectively, it occurs in the middle of the signal period. By the same factor the other time points between 740 and 742 and, respectively between 750 and 752, are extended. The period of the signal pulse 702 is shifted and extended for the transformation into the signal pulse 712 in such manner that the time point 732 is shifted so that, as is the case with time point 742, it occurs in the middle of the signal period. The time point 734, for the transformation into the time point 744, is shifted first by the same value by which also the time point 732 was shifted in the transformation into the time point 742, and thereupon the time course between the time points is extended so that the signal pulse lasts for exactly half a signal period. All the time points between 732 and 734 are shifted and extended in the same manner in order to be transformed into the time points between 742 and 744. The time course of the signal pulse 703 is shifted and extended for the transformation into the signal pulse 722 in such manner that the time point 734 is shifted to occur in the middle of the signal period. The time point 36 remains in the transformation into the time point 754 at the end of the signal period. The time course between the time points 734 and 736 is then extended so that the signal pulse lasts half a signal period. All the time points between 734 and 736 are likewise shifted and extended in the same manner in order to be transformed into the time points between 752 and 754.

The subdivision of the curve 700 into the curves 710 and 720 occurs with a phase shift of 360°. First, data corresponding to the curve 700 is stored in a temporary (intermediate) storage, in order to be subdivided in the signal period following thereupon into the two curves 710 and 720.

Measurement Value Formation

Figure 24:
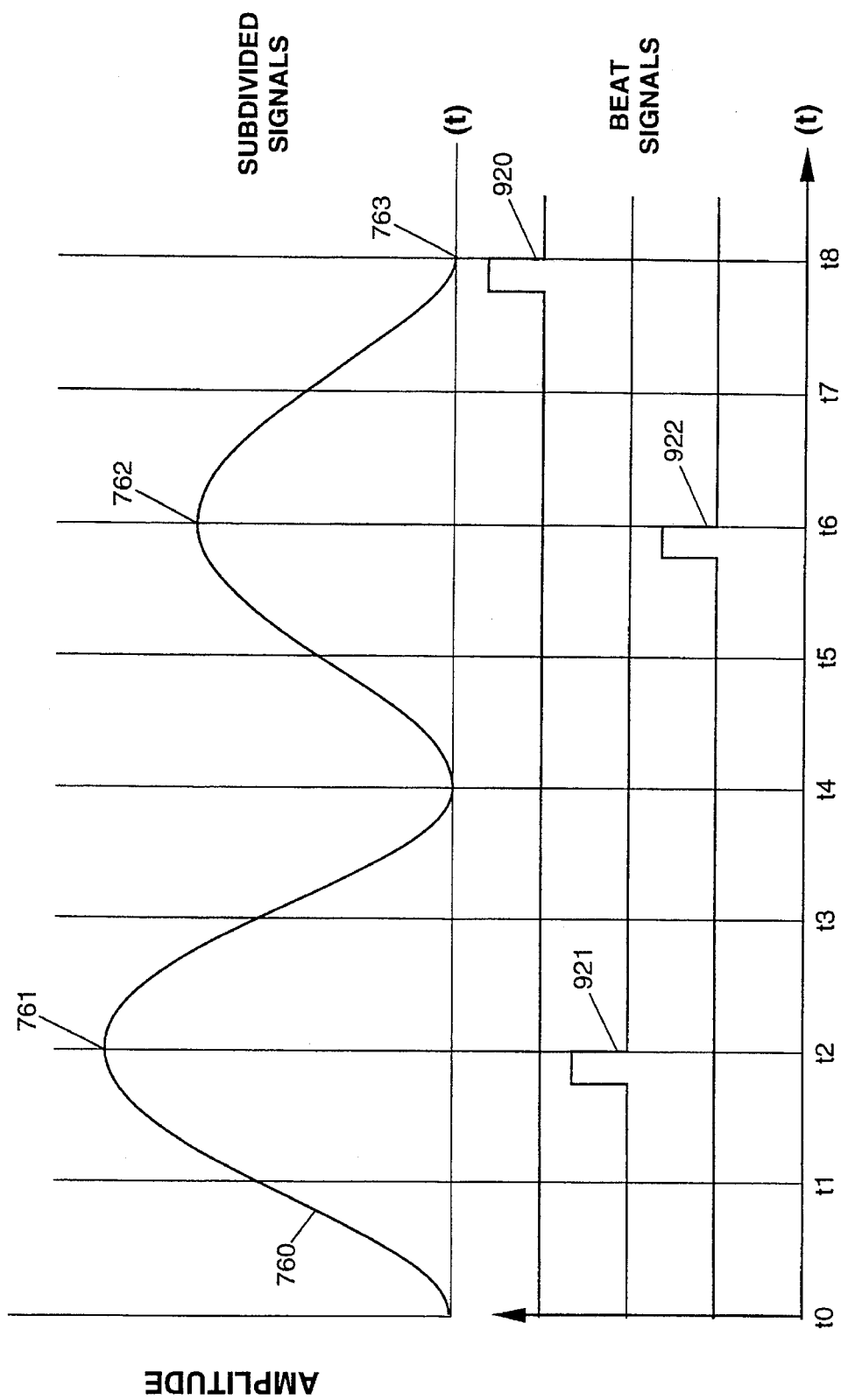
FIG. 24 is a further timing diagram that shows the relation between the detector signals and generated beat signals.

FIG. 24 shows the time relation between the signals 13, 23, 14 and 24 and the beat signals 920, 921 and 922. The curve 760 represents an idealized waveform of the signals 13, 23, 14 and 24. The curves 710 and 720 of FIG. 23 represent similar waveforms.

The falling edge of beat signal 921 corresponds to the middle 761 of the first pulse of the curve 760. The falling edge of beat signal 922 corresponds to the middle 762 of the second pulse of the curve 760. The falling edge of beat signal 920 corresponds to the end of the signal period of the curve 763.

Signal Evaluation

Figure 25:
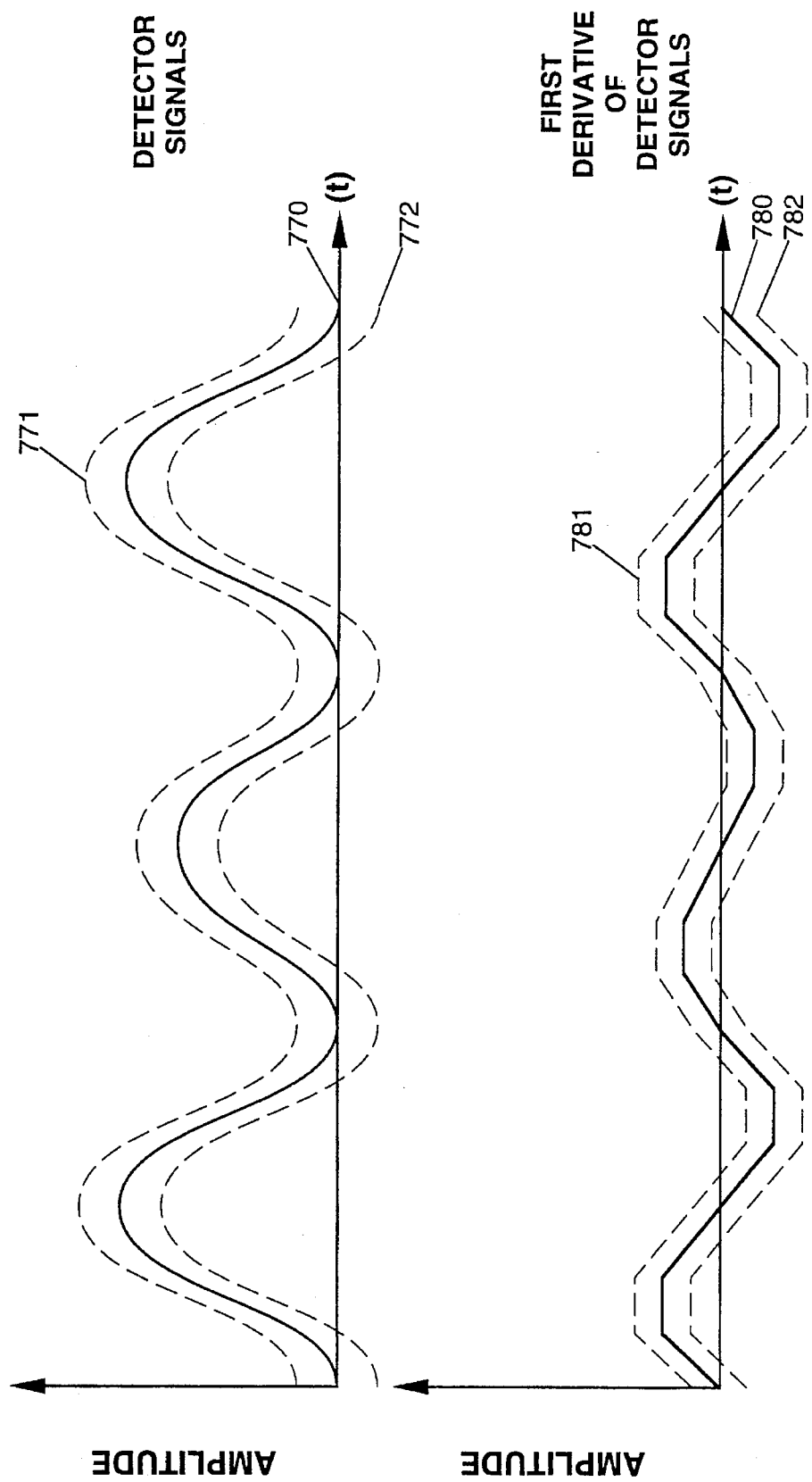
FIG. 25 is a graphical representation of an idealized curve of the detector signals within tolerance limits.

FIG. 25 shows the idealized waveforms of the signals 11, 21, 31, 41, 12, 22, 32 and 42, their tolerance limits, and the first derivative of those signals with tolerance limits. Those skilled in the-art will understand that the tolerance limits are not necessarily to scale.

The curve 770 represents the idealized waveform of a signal period of the signals 11, 21, 31, 41, 12, 22, 32 and 42. The curves 771 and 772 represent the tolerance range within which those signals must be detected.

The curve 780 represents the idealized waveform of a signal period of the first derivative of the signals 11, 21, 31, 41, 12, 22, 32 and 42. The curves 781 and 782 represent the tolerance range within which the first derivative of the signals must be detected.

Measurement Value Formation

Figure 26:
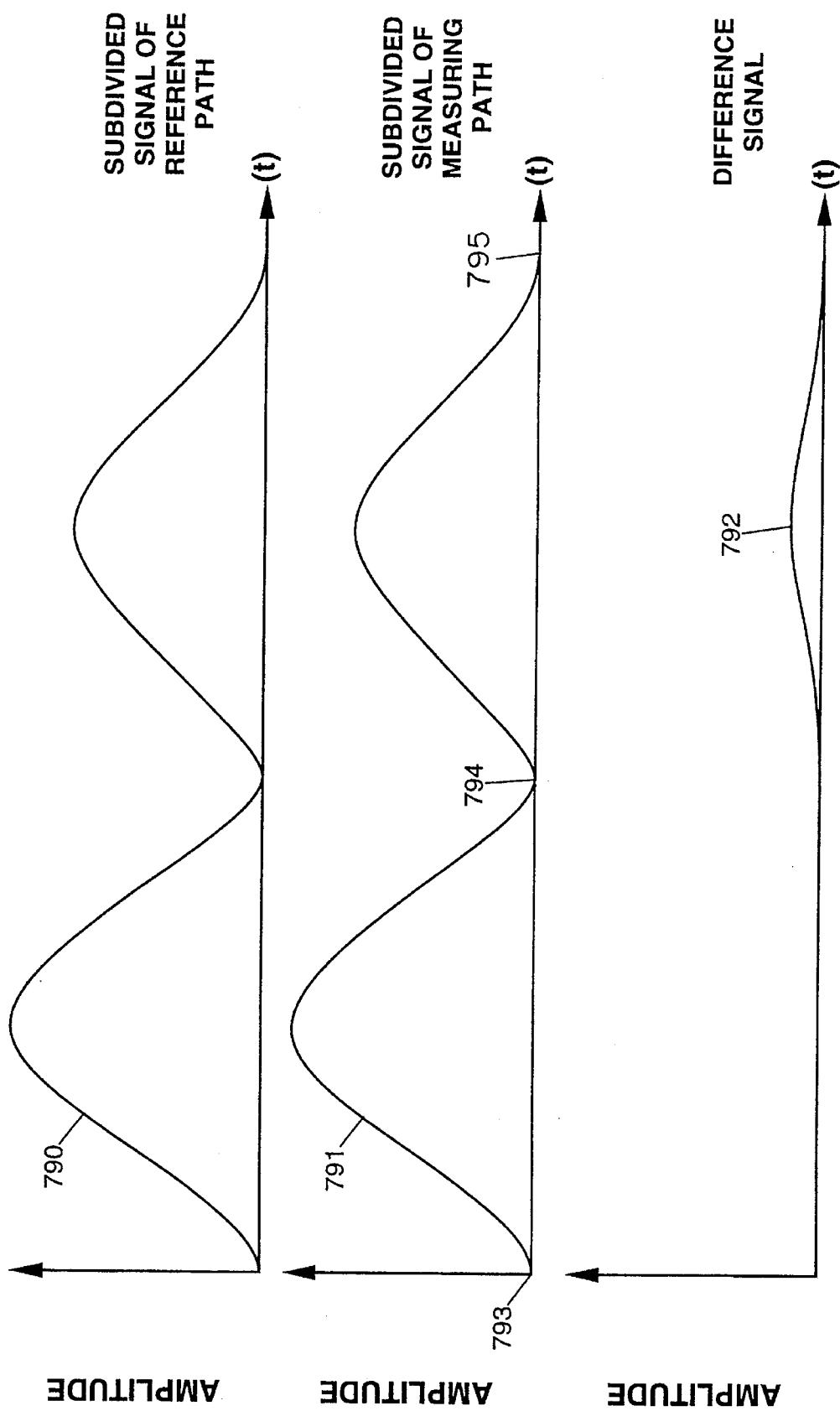
FIG. 26 is a graphical representation of an idealized curve of the measurement value formation.

FIG. 26 shows the idealized waveforms for the measurement value formation. The curve 790 corresponds to the signals 23 and 24. The curve 791 corresponds to the signals 13 and 14. The curve 792 corresponds to the signals 160 and 260. In the first half of the signal period, the two signals denoted by 790 and 791 are identical between the time points 793 and 794. The difference signal, the curve 792, is consequently zero. Between the time points 794 and 795, the curve 791 is damped due to the characteristic absorption on the measuring path 5, and a small difference arises. The frequency of the difference signal corresponds to half the pulse repetition frequency in the curves 790 and 791.

Other Alternative Embodiments

Those skilled in the art will appreciate that the invention is not limited to the specific embodiments described herein upon consideration of the foregoing teachings. For example, the following alternatives may be employed. Instead of the automatic level equalization between the signals 12 and 22 in the amplifier and filter circuit 501, it is also possible to determine the level differences between the signals 12 and 22 during the uncharacteristic signal pulse and thereupon to correct the measurement value.

Figure 27:
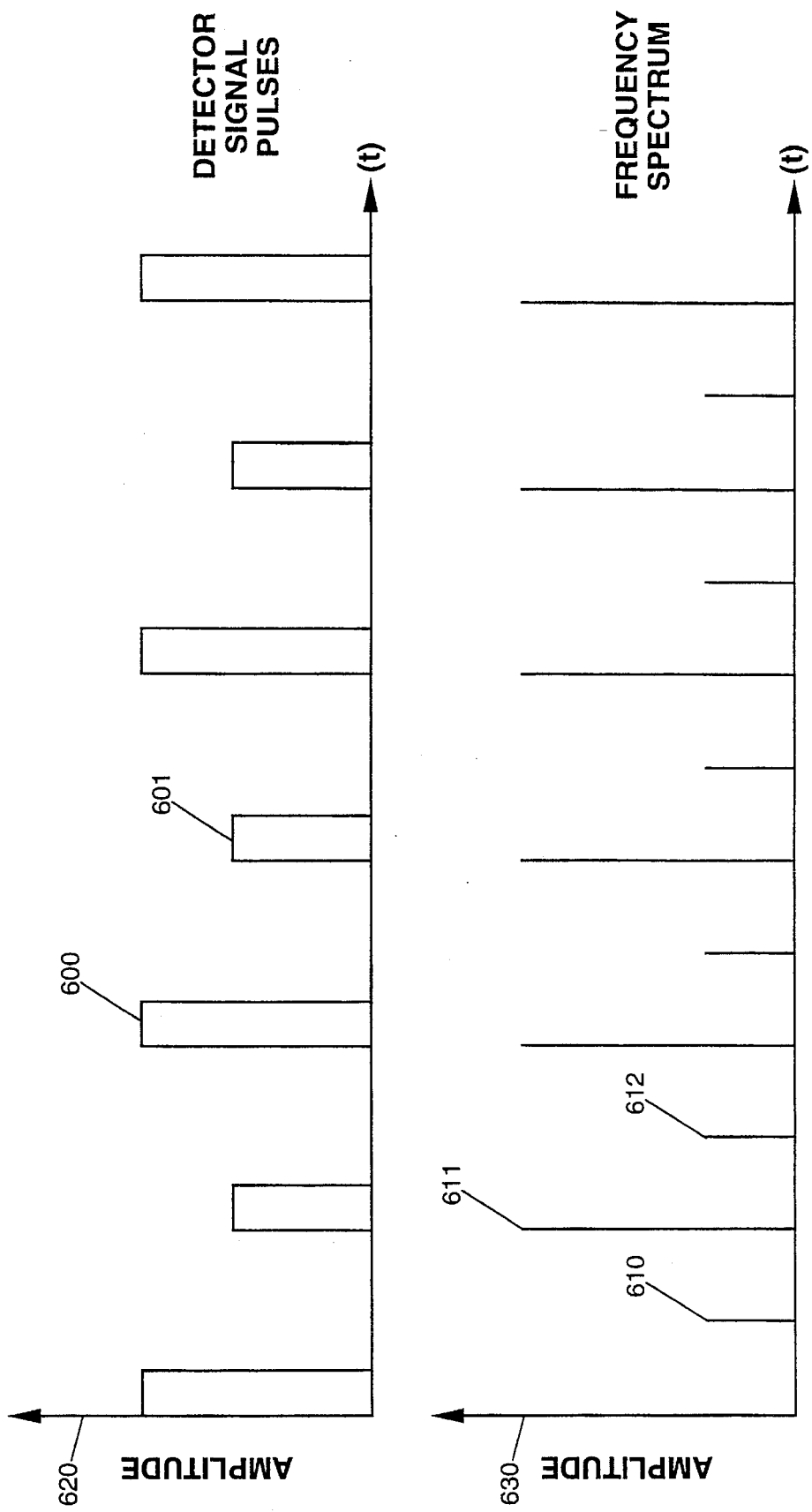
FIG. 27 is a graphical representation of an idealized detector signal and the corresponding Fourier spectrum.

FIG. 27 shows an alternative beam source stabilization scheme. In particular, the idealized output signals 11, 21, 31 or 41 of a detector 10, 20 30 or 40 in the time domain 620 and the frequency spectrum 630 of these signals are shown. The signal pulse 600 is developed from the uncharacteristic light pulse. The signal pulse 601 is developed from the characteristic light pulse. The spacing between the signal pulses is constant.

When the signal 620 is subjected to a Fourier analysis, the spectrum 630 yielded is shown in FIG. 27. The spectral line 611 corresponds to the pulse repetition frequency of the light pulses. The spacing of the spectral lines 610 and 611 corresponds to half the pulse repetition frequency. Accordingly, the spectral line 610 corresponds to half the pulse repetition frequency. The spacing of the spectral lines 611 and 612 corresponds to half the pulse repetition frequency. The spectral line 612, accordingly, corresponds to one-and-a-half times the pulse repetition frequency.

The height of the spectral line 610 or 612 is dependent on the damping of the characteristic light pulse on the measuring path 5. If the light beam is not damped and the laser emits an ideal light signal, the spectral lines 610 and 612 and all the other odd spectral lines result. If the characteristic light pulse is completely absorbed on the measuring path 5, then the signal 620 consists only of the characteristic signal pulse(s) 601. Accordingly, the spectral line 611 vanishes in the spectrum.

The spectral lines are repeated in dependence on the actual waveform of the detector signal in the time domain and on the transfer function of the detector. The information content of the spectrum remains unaltered. For evaluation, the relation of any arbitrary pair of spectral lines can be utilized.

The method in accordance with the invention is not limited to a laser source of radiation. Any radiation source that emits radiation characteristic for a substance can be used. The radiation used, however, must be are detected and converted to an electrical signal proportional to the impinging radiation energy.

What is claimed is:

1. A method for evaluating characteristic absorption of one or more substances in a mixture comprising:

applying radiation pulses generated by a radiation source to a measuring path including the mixture therein and to a reference path excluding the mixture therefrom, the radiation pulses having in alternation (i) at least one characteristic wavelength pulse with a wavelength characteristic of one substance being evaluated, and (ii) an uncharacteristic wavelength pulse with a wavelength uncharacteristic of the substance being evaluated;

detecting the radiation pulses applied to the measuring path and the reference path;

converting the detected pulses into a measuring path signal and a reference path signal; and deriving a measurement signal from the difference between the measuring path signal and the reference path signal.

2. The invention as in claim 1 further including deriving a difference signal indicative of the difference between the measuring path signal and the reference path signal; and signal conditioning the difference signal as a function of, selectively, frequency and time, and evaluating the difference signal to provide the measurement signal.

3. The invention as in claim 2, wherein the measurement signal is derived from a difference between the difference signal at the interval of the maximum of the characteristic wavelength pulse and the difference signal at the interval of the maximum of the uncharacteristic wavelength pulse.

4. The invention according to claim 1 further comprising:

comparing the measuring path signal with a selected reference value;

altering the measuring path signal upon a deviation from the reference value;

comparing the reference path signal with a selected reference value; and altering the reference path signal upon a deviation from the reference value.

5. The invention of claim 1 further including subdividing the reference path signal and measuring path signal into a plurality of signal pairs, each of the signal pairs comprising a first signal pulse corresponding to the characteristic wavelength and a second signal pulse corresponding to the uncharacteristic wavelength.

6. The invention as in claim 5 further including applying said radiation pulses to at least one calibration path containing a known concentration of the substance being evaluated and deriving a calibration path signal; and applying the reference path signal and the calibration path signal to a radiation source stabilization circuit for stabilizing the radiation source.

7. The method of claim 6 wherein the reference path signal and the calibration path signal are time-selectively sampled in order to determine the phase position, the maximal value and the average value of the radiation pulses for a signal period.

8. The invention as in claim 7 further including applying a control signal to the radiation source; and altering the control signal upon the detection of variations in the reference path signal and the calibration path signal.

9. The invention as in claim 1 further including detecting the concentration of a second substance in the mixture to which the substance being evaluated has a cross-sensitivity and providing a concentration output signal indicative of the concentration of the second substance; and correcting the measurement signal in response to the concentration output signal of the second substance.

10. The invention according to claim 1 further comprising:

comparing the measuring path signal with the reference path signal;

altering the measuring path signal upon a deviation from a reference value given by the reference path signal.

11. Apparatus for evaluating characteristic absorption of one or more substances in a substance mixture comprising:

means for generating in a signal period radiation pulses having in alternation at least one characteristic wavelength pulse with a wavelength characteristic of one substance to be measured and an uncharacteristic wavelength pulse with a wavelength uncharacteristic of the substance to be measured;

a measuring path containing the substance mixture therein including detecting means for detecting the radiation pulses transmitted through the measuring path and providing a measuring path signal;

a reference path excluding the substance mixture therefrom including detection means for detecting said radiation pulses transmitted through the reference path and providing a reference path signal; and means for deriving a measurement value from the difference between said measuring path signal and said reference path signal.

12. Apparatus as in claim 11, further including:

a calibrating path containing a known concentration of the substance being evaluated and including detecting means for detecting the radiation pulses transmitted through the calibration path and providing a calibration path signal; and means for time-selectively sampling the reference path signal and the calibration path signal for determining the phase position, the maximum value, and the average value of the radiation pulses in a signal period.

13. A method for determining the concentration of a first substance in a mixture by evaluating characteristic light absorption thereof, the first substance having a cross-sensitivity to a second substance in the mixture, the method comprising:

generating a sequence of radiation pulses including in alternation an uncharacteristic wavelength pulse having a wavelength uncharacteristic of the first and second substances, a first characteristic wavelength pulse having a wavelength characteristic of the first substance, and a second characteristic wavelength pulse having a wavelength characteristic of the second substance;

applying the sequence of radiation pulses to a measuring path including the mixture therein;

applying the sequence of radiation pulses to a reference path excluding the mixture therefrom;

detecting the sequence of radiation pulses applied to the measuring path and the reference path and converting the detected pulses into, respectively, a measuring path signal and a reference path signal;

amplifying the measuring path signal and the reference path signal to equalize respective portions of the measuring path signal and the reference path signal corresponding to the uncharacteristic wavelength pulse;

comparing the reference path signal to stored values and, in case of deviation, applying identical corrections to the reference path signal and the measuring path signal;

deriving a first measurement signal indicative of the concentration of the first substance in the mixture from the difference between the measuring path signal and the reference path signal.

14. The method as in claim 13, wherein the step of deriving the first measurement signal includes:

deriving a difference signal indicative of the difference between the measuring path signal and the reference path signal;

signal conditioning the difference signal as a function of, selectively, frequency and time; and determining the difference between a value of the difference signal at an interval corresponding to a maximum of the first characteristic wavelength pulse and a value of the difference signal at an interval corresponding to the maximum of the uncharacteristic wavelength pulse to provide the first measurement signal.

15. The method as in claim 14, further including the step of deriving a second measurement signal indicative of the concentration of the second substance in the mixture from the difference between the measuring path signal and the reference path signal, and the step of correcting the first measurement signal for cross-sensitivity due to the concentration of the second substance.

16. The method as in claim 14, wherein the step of deriving the first measurement signal includes subdividing each of the reference path signal and the measuring path signal into two signal pairs, each signal pair comprising a first signal pulse corresponding to the uncharacteristic wavelength pulse and a second signal pulse corresponding to one of the first and second characteristic wavelength pulses.

17. The method as in claim 13, wherein the step of comparing the reference path signal to the stored values is performed digitally.

18. The method as in claim 13, further including applying the sequence of radiation pulses to a first calibration path containing a known concentration of the first substance and deriving a first calibration path signal;

applying the sequence of radiation pulses to a second calibration path containing a known concentration of the second substance and deriving a second calibration path signal;

sampling the reference path signal and the first and second calibration path signals to generate an output signal for controlling the radiation source.

19. The method as in claim 18, wherein the step of sampling comprises time-selectively sampling the reference path signal and the first and second calibration path signals for determining the phase position, the maximal value and the average value of the radiation pulses.

* * * * *